(12) United States Patent
White et al.

(10) Patent No.: US 11,850,166 B2
(45) Date of Patent: Dec. 26, 2023

(54) SYSTEMS AND METHODS FOR AN EXPANDABLE INTERBODY DEVICE

(71) Applicant: Dignity Health, San Francisco, CA (US)

(72) Inventors: Michael D. White, San Francisco, CA (US); Dakota Graham, San Francisco, CA (US)

(73) Assignee: Dignity Health, San Francisco, CA (US)

( * ) Notice: Subject to any disclaimer, the term of this patent is extended or adjusted under 35 U.S.C. 154(b) by 0 days.

(21) Appl. No.: 18/042,319

(22) PCT Filed: Sep. 1, 2021

(86) PCT No.: PCT/US2021/048689
§ 371 (c)(1),
(2) Date: Feb. 21, 2023

(87) PCT Pub. No.: WO2022/051380
PCT Pub. Date: Mar. 10, 2022

(65) Prior Publication Data
US 2023/0240860 A1    Aug. 3, 2023

Related U.S. Application Data

(60) Provisional application No. 63/073,142, filed on Sep. 1, 2020.

(51) Int. Cl.
*A61F 2/44* (2006.01)
*A61F 2/28* (2006.01)
*A61F 2/30* (2006.01)

(52) U.S. Cl.
CPC ........ *A61F 2/447* (2013.01); *A61F 2002/285* (2013.01); *A61F 2002/30406* (2013.01);
(Continued)

(58) Field of Classification Search
CPC ...... A61F 2/44; A61F 2/447; A61F 2002/285; A61F 2002/30406; A61F 2002/30518; A61F 2002/30525; A61F 2002/30624
(Continued)

(56) References Cited

U.S. PATENT DOCUMENTS

| 8,114,131 B2 | 2/2012 | Kohm et al. |
| 8,920,505 B2 | 12/2014 | Aferzon et al. |

(Continued)

OTHER PUBLICATIONS

Patent Cooperation Treaty, International Search Report and Written Opinion, International Application No. PCT/US2021/048689, dated Dec. 15, 2021, 10 pages.

*Primary Examiner* — Jessica Weiss
(74) *Attorney, Agent, or Firm* — Polsinelli PC

(57) ABSTRACT

Various embodiments of an expandable interbody cage device configured to reduce subsidence into an endplate of a vertebral body by including a plurality of arms that engage the cortical tissue of the vertebral body. The plurality of arms increase the surface area and improve distribution of force, especially around stronger parts of the endplate such as the cortical bone at the rim of the endplate. The expandable interbody cage device maintains a low or slim profile while in a "closed" configuration during insertion between vertebrae and is further operable to laterally expand into an "open" configuration that increases the surface area of the expandable interbody cage device after insertion to securely engage the expandable interbody cage device between the vertebra. The expandable interbody cage device further includes one or more ports and/or cavities in which bone graft material can be disposed within.

19 Claims, 20 Drawing Sheets

(52) U.S. Cl.
CPC ............. *A61F 2002/30518* (2013.01); *A61F 2002/30525* (2013.01); *A61F 2002/30624* (2013.01)

(58) Field of Classification Search
USPC ................. 623/17.11–17.16; 606/99–100
See application file for complete search history.

(56) References Cited

U.S. PATENT DOCUMENTS

| | | | |
|---|---|---|---|
| 2005/0049590 A1* | 3/2005 | Alleyne | A61F 2/442 606/279 |
| 2006/0095136 A1* | 5/2006 | McLuen | A61F 2/4455 623/17.11 |
| 2007/0270961 A1* | 11/2007 | Ferguson | A61F 2/4425 623/17.11 |
| 2012/0004732 A1* | 1/2012 | Goel | A61F 2/447 623/17.16 |
| 2012/0209386 A1* | 8/2012 | Triplett | A61F 2/4465 623/17.16 |
| 2013/0245767 A1 | 9/2013 | Lee et al. | |
| 2014/0052253 A1* | 2/2014 | Perloff | A61F 2/447 623/17.15 |
| 2020/0246157 A1* | 8/2020 | Berry | A61F 2/447 |
| 2021/0045891 A1* | 2/2021 | Rogers | A61F 2/4455 |
| 2021/0068973 A1* | 3/2021 | McLuen | A61F 2/30 |
| 2021/0315709 A1* | 10/2021 | Barnes | A61F 2/4425 |

* cited by examiner

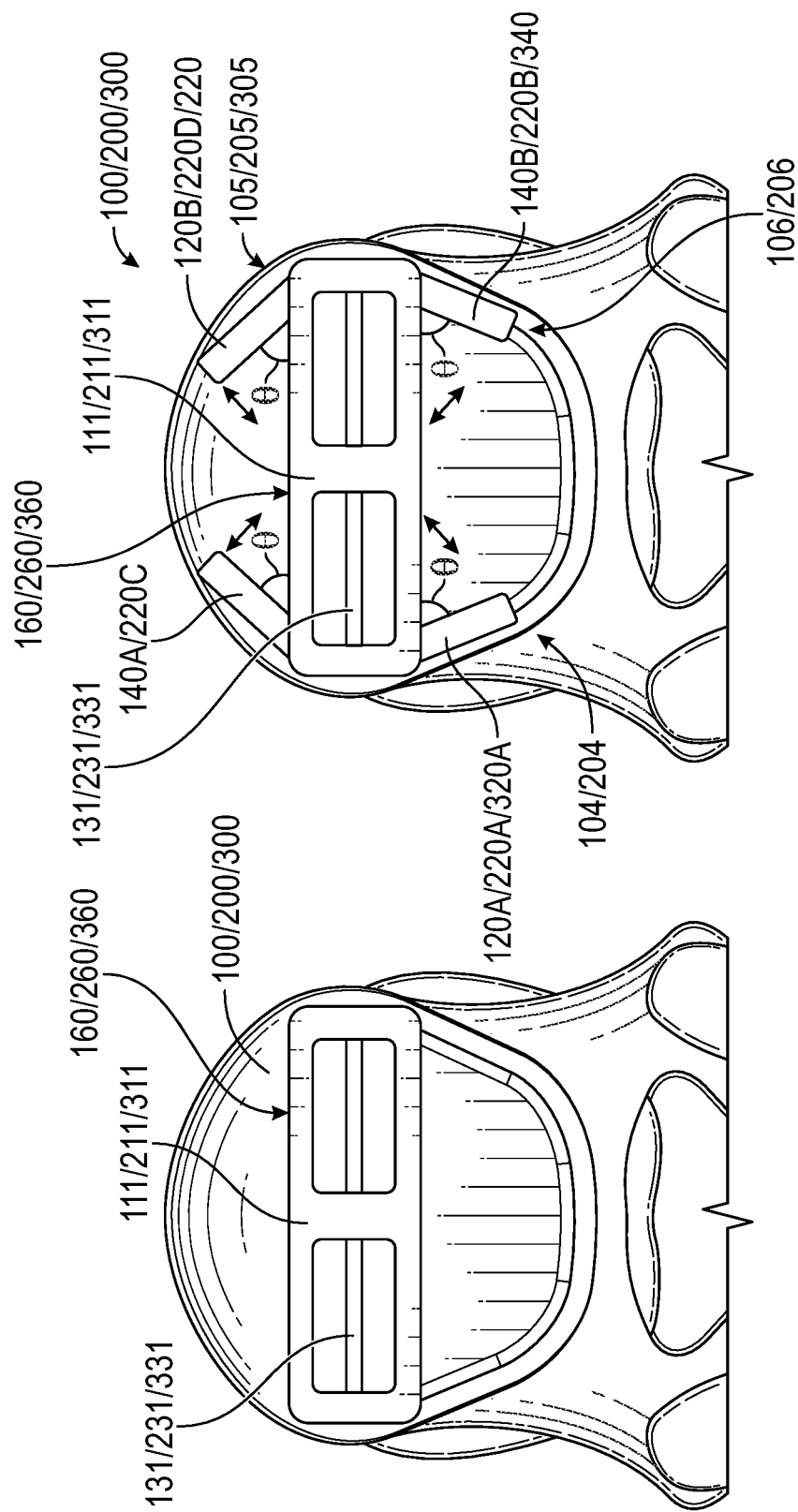

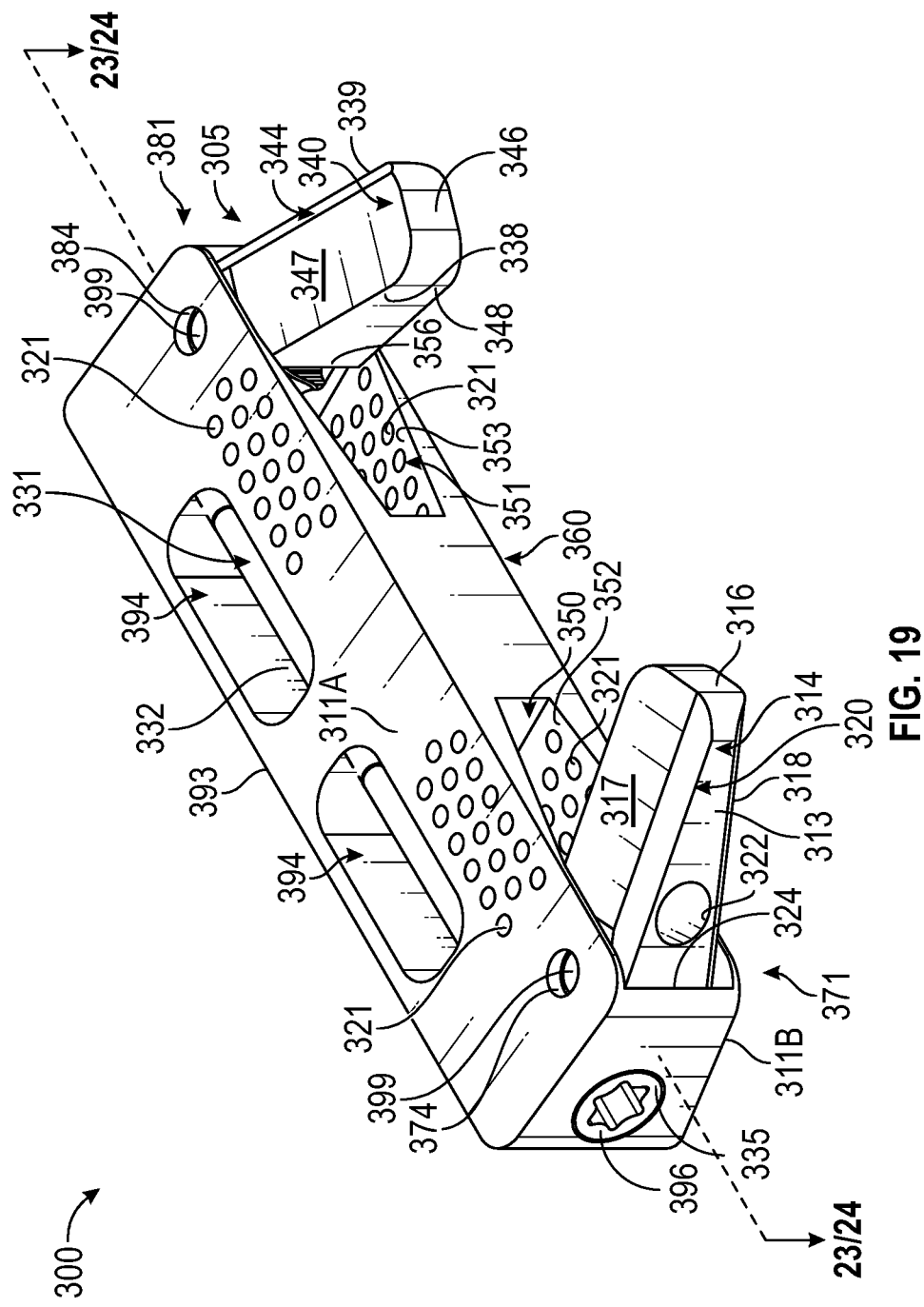

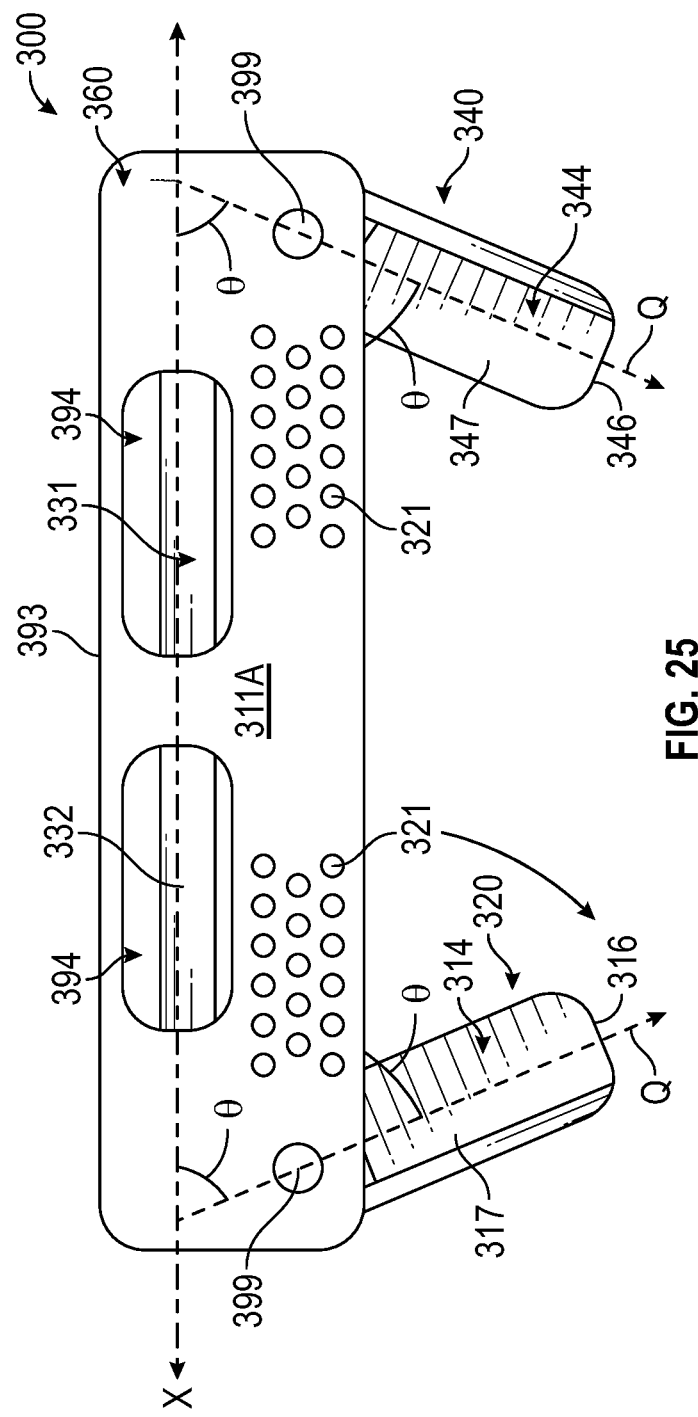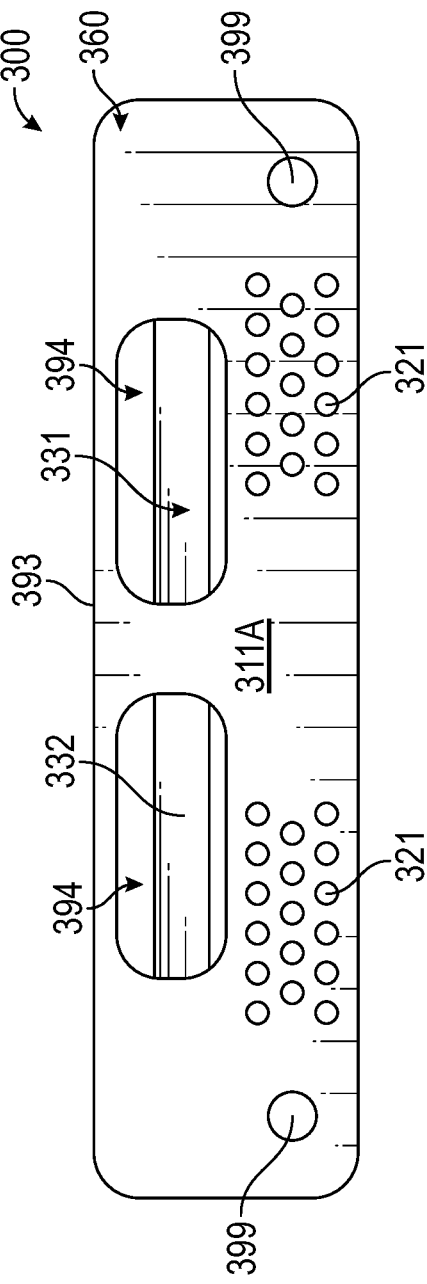

SYSTEMS AND METHODS FOR AN EXPANDABLE INTERBODY DEVICE

FIELD

The present disclosure generally relates to interbody fusion devices, and in particular, to a system and associated method for an expandable interbody device for lateral lumbar interbody fusion procedures.

BACKGROUND

For interbody fusions such as the lateral lumbar interbody fusion (LLIF), decompression of neural elements occurs indirectly by increasing the height of the disc space, therefore opening up the neural foramen. One of the major complications of placing an interbody cage is the risk for development of subsidence, which is sinking of the interbody cage into the vertebral body (FIG. 1A shows normal placement of an interbody cage and FIG. 1B demonstrates subsidence of the interbody cage into the spongy cancellous bone tissue of the vertebral body). This causes loss of disc height and loss of the indirect decompression achieved with surgery, and ultimately a return of symptoms and need for reoperation. Previous research has demonstrated that using wider grafts reduces the risk and grade of subsidence. This is thought to occur due to increased surface area to distribute axial forces, as well as a wider graft taking advantage of the stronger cortical bone around the edge of an endplate of the vertebral body. Biomechanical studies have demonstrated that the cortical bone around the endplate is much stronger than the cancellous bone within the middle of the endplate.

It is with these observations in mind, among others, that various aspects of the present disclosure were conceived and developed.

BRIEF DESCRIPTION OF THE DRAWINGS

FIGS. 2A-2D are illustrations showing placement of an expandable interbody cage device on a surface of a vertebral body;

FIG. 19 is a perspective view of a third embodiment of the expandable interbody cage device of FIGS. 2A and 2B shown in an open configuration;

FIG. 25 is a top plan view of the expandable interbody cage device of FIG. 19 shown in the open configuration; and FIG. 26 is a top plan view of the expandable interbody cage device of FIG. 19 shown in a closed configuration.

Corresponding reference characters indicate corresponding elements among the view of the drawings. The headings used in the figures do not limit the scope of the claims.

DETAILED DESCRIPTION

Figure 1A:
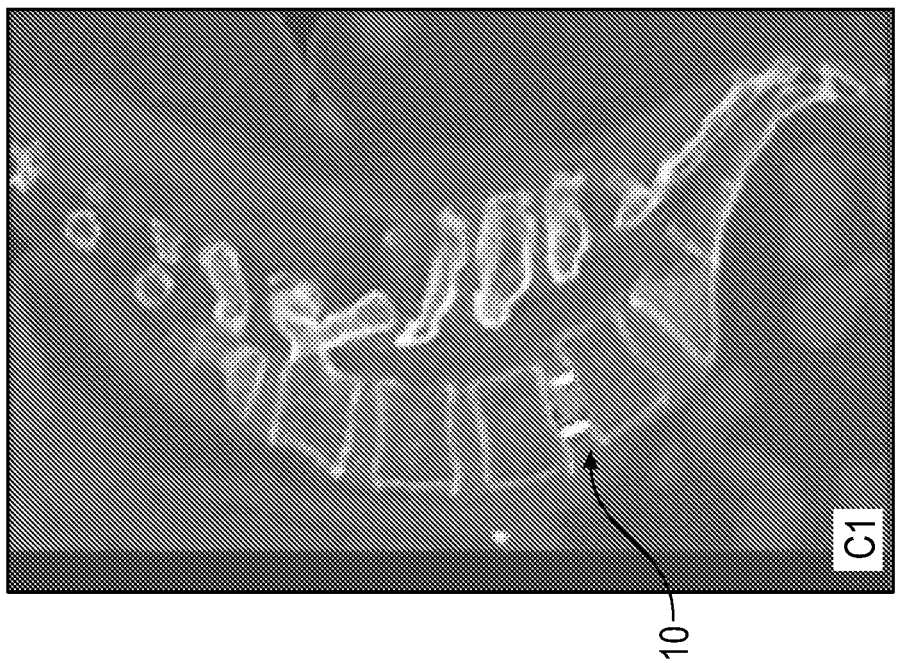
FIGS. 1A and 1B are respective images showing normal placement of an interbody cage device and abnormal subsidence of the placed interbody cage into the vertebral body.

Various embodiments of an expandable interbody cage device for interbody fusions such as a lateral lumbar interbody fusion are disclosed herein. In particular, the expandable interbody cage device is configured to reduce subsidence of the expandable interbody cage device into an endplate of a vertebral body by including a plurality of arms that engage the cortical tissue of the vertebral body to increase the surface area and improve distribution of force, especially around stronger parts of the endplate such as the cortical bone at the rim of the endplate. The expandable interbody cage device maintains a low or slim profile while in a "closed" configuration during insertion between vertebrae and is further operable to laterally expand into an "open" configuration that increases the surface area of the expandable interbody cage device after insertion to securely engage the expandable interbody cage device between the vertebrae. The arms enable the expandable interbody cage device to rest on the cortical bone at an edge of the endplate rather than on spongy cancellous bone in a center of the endplate. In some embodiments, dimensions of the expandable interbody cage device while in the open configuration are variable, enabling a practitioner to adapt to vertebrae of varying sizes and ensuring that the expandable interbody cage device securely engages the cortical bone of the vertebral body. The expandable interbody cage device further includes one or more ports and/or cavities in which bone graft material can be disposed within. Referring to the drawings, embodiments of an expandable interbody cage device are illustrated and generally indicated as 100, 200 and 300 in FIGS. 1-26.

Figure 1B:
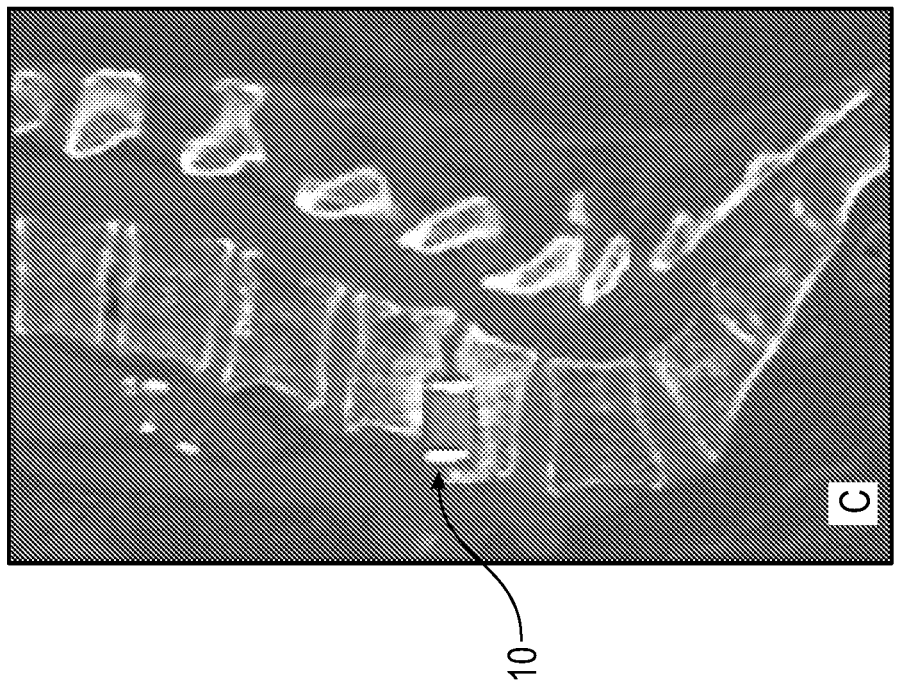
Figure 2D:
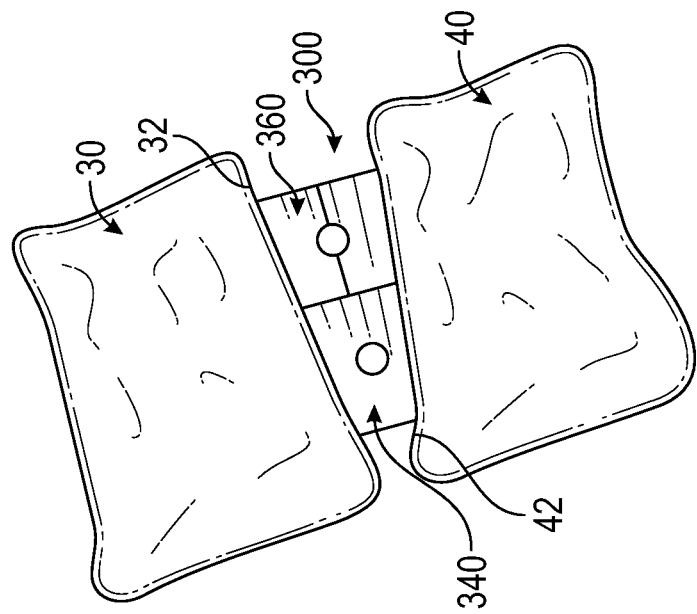
Figure 2C:
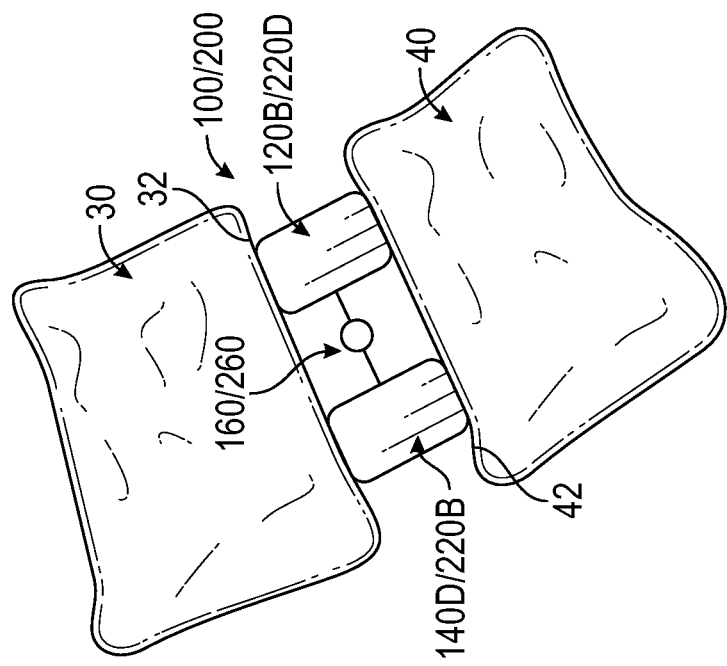

A common problem with conventional interbody cage devices is subsidence, which is the tendency of the interbody cage device to sink into the cancellous bone tissue in the middle of an endplate of a vertebra. The endplate of the vertebra includes spongy cancellous tissue towards the middle of the endplate and hardened cortical tissue towards the edges of the endplate. FIG. 1A is an image showing proper placement of a conventional interbody cage device between vertebrae. Interbody cage devices are often packed with bone graft material to encourage bone growth and eventual fusion of the vertebrae. However, even with initially proper implantation of some interbody cage devices, subsidence can still occur as the conventional interbody cage device becomes compressed by the spine into the cancellous tissue of the endplate over time, as shown in FIG. 1B. This can especially happen if the interbody cage device is not secure and immovable between the vertebrae.

The expandable interbody cage devices 100/200/300 are intended to address this issue. As shown in FIGS. 2A-2D, the expandable interbody cage devices 100/200/300 includes a respective cage assembly 160/260/360 that increases a height of a disc space between vertebrae when installed between adjacent vertebrae within a body. Each cage assembly 160/260/360 is associated with a respective plurality of arms 105/205/305 that each include a respective first pair of arms 104/204 and a second respective pair of arms 106/206 or at least a respective first arm 120A/220A/320 and a respective second arm 140B/220B/340 associated with a respective axle 131/231/331. The respective first arm 120A/220A/320 and a respective second arm 140B/220B/340 are operable for each expandable interbody cage device 100/200/300 to assume an open configuration (FIG. 2B) that increases the surface area of each expandable interbody cage device 100/200/300 across the endplate of the vertebra, as shown. In a preferred embodiment, the each of the arms 105/205/305 of the respective expandable interbody cage device 100/200/300 engages the endplate on or closer towards the edges to better distribute force across the cortical bone of the endplate rather than the cancellous bone in the center of the endplate. In some embodiments, as will be discussed in greater detail below, the arms 105/205/305 can be opened at a variable arm angle θ to accommodate differences in anatomy.

In general, each of the expandable interbody cage devices 100/200/300, when in a closed configuration shown in FIG. 2A, maintains a small profile for insertion between two adjacent vertebrae. Smaller devices are generally easier and safer to implant, as interbody devices are usually hammered in between vertebrae. Upon each of the expandable interbody cage devices 100/200/300 assuming the open configuration shown in FIG. 2B, a greater surface area across the endplate of the vertebra is achieved for improved force distribution and stability when each of the expandable interbody cage devices 100/200/300 is inserted between the vertebrae. In addition, each of the expandable interbody cage devices 100/200/300 can include one or more bone graft material cavities, such as bone graft material cavity 194 (FIGS. 5-6), that can be packed with bone graft material, or can further include one or more bone graft material ports such as bone graft material ports 222/332 (FIGS. 14 and 19) for post-insertion packing of bone graft material into the interbody space. Each of the expandable interbody cage devices 100/200/300 enables the bone graft material to contact a larger surface area of the endplate to encourage even distribution of bone growth throughout the interbody space for successful fusion of the joint while increasing the height of the disc space.

In one method of operation, each of the expandable interbody cage devices 100/200/300 may be first inserted into an interbody space between two adjacent vertebrae while in a closed configuration. In particular, the expandable interbody cage devices 100/200/300 may be hammered between a first vertebra 30 and a second vertebra 40 (FIGS. 2C and 2D) such that the expandable interbody cage devices 100/200/300 contacts the endplate surfaces 32 and 42 of both vertebrae 30 and 40. Upon verification of proper placement (most commonly with intraoperative x-ray) the practitioner opens the plurality of arms 105/205/305 for a respective expandable interbody cage device 100/200/300 to an open configuration (FIG. 2B) by rotating the respective axle 131/231/331 in a clockwise or counterclockwise direction C or D. Rotation of each axle 131/231/331 results in rotation of the respective plurality of arms 105/205/305 outwardly in a clockwise or counterclockwise direction A or B away from each respective axle 131/231/331. In some embodiments, components of the expandable interbody cage device 100 can be made of titanium, Polyetheretherketone PEEK, or any other suitable material for an interbody device.

Figure 3:
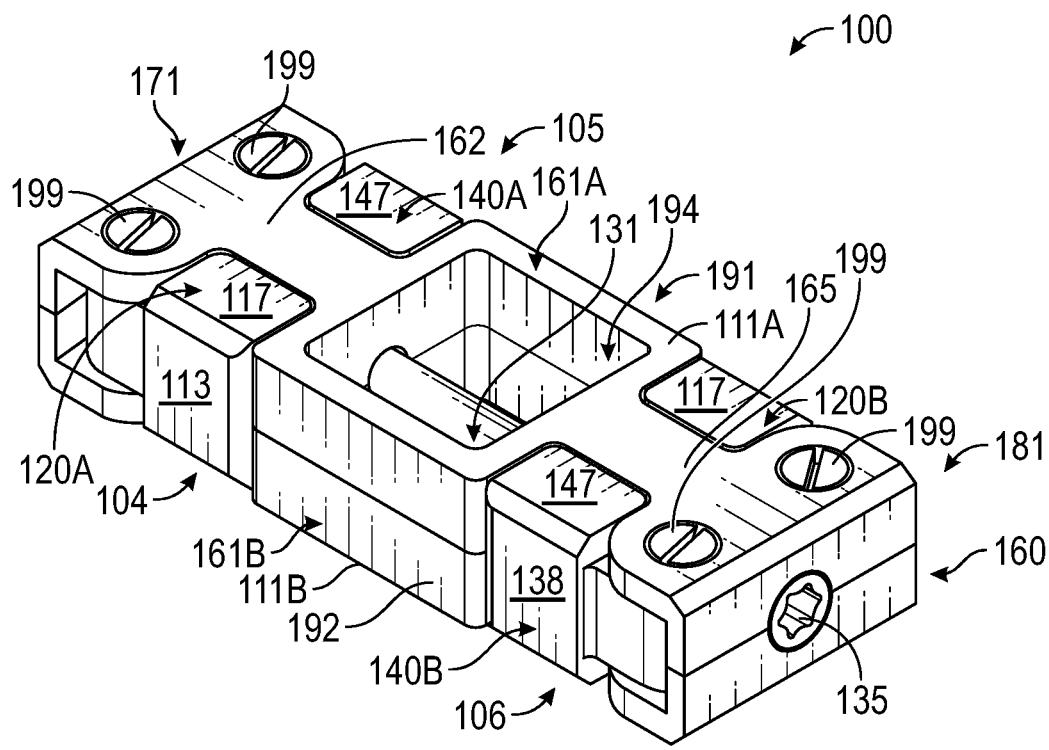
FIG. 3 is a perspective view of one embodiment of the expandable interbody cage device of FIGS. 2A and 2B shown in a closed configuration.
Figure 4:
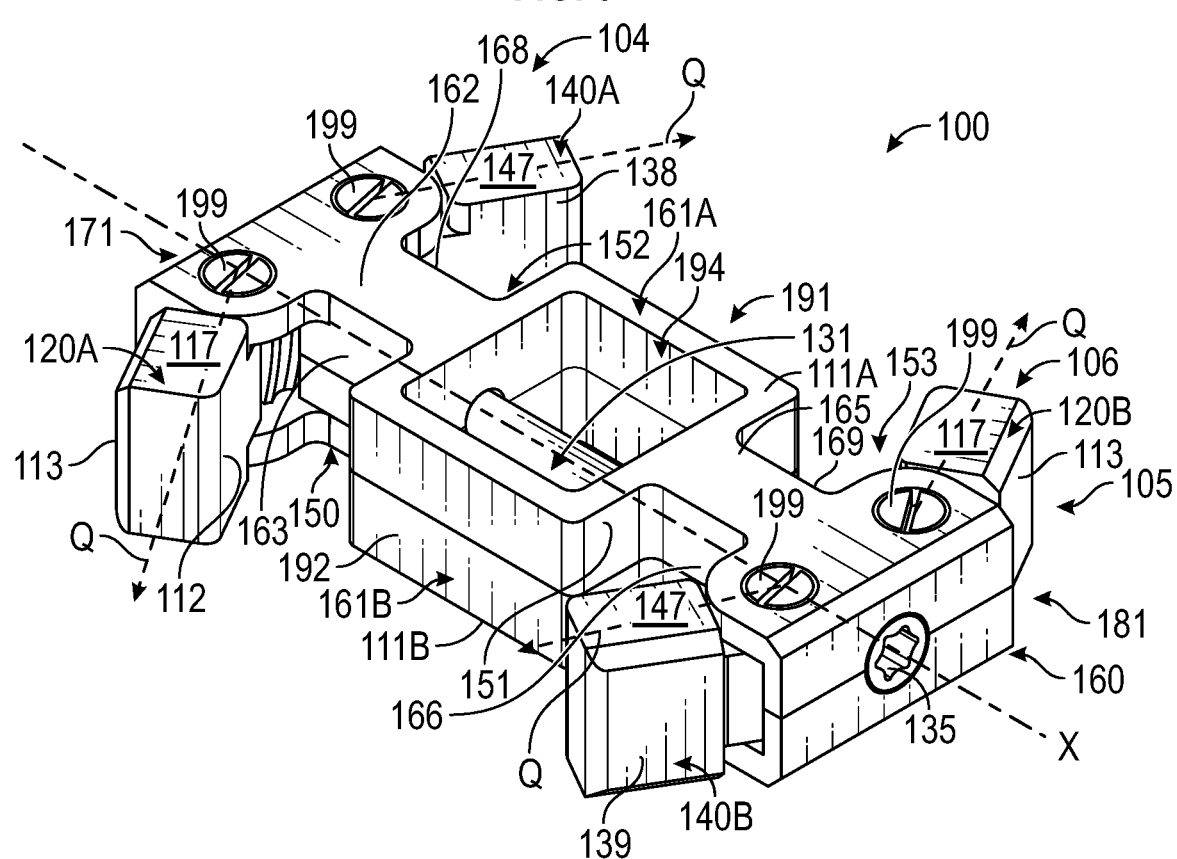
FIG. 4 is a perspective view of the expandable interbody cage device of FIG. 3 shown an open configuration.
Figure 5:
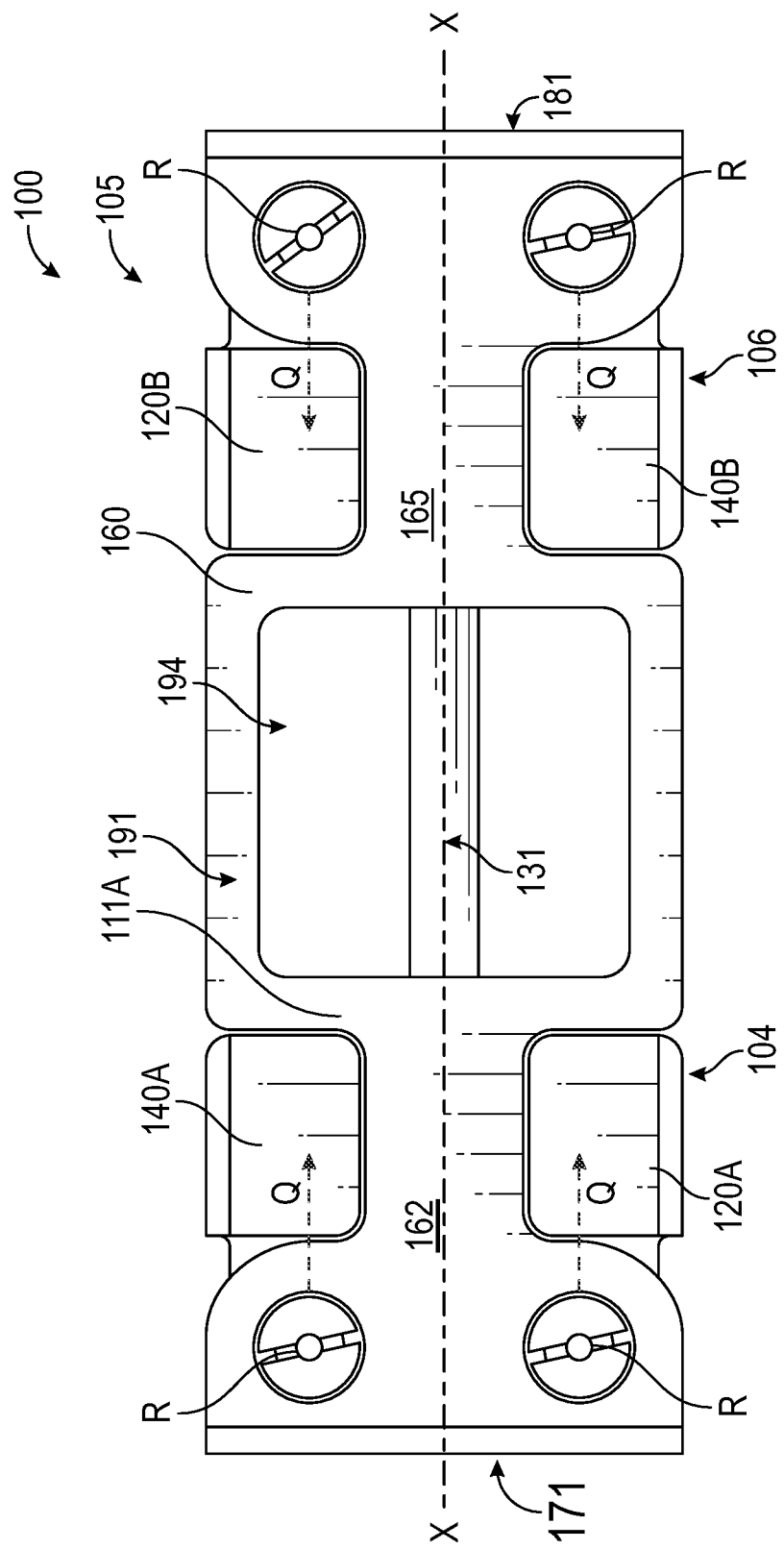
FIG. 5 is a top plan view of the expandable interbody cage device of FIG. 3 shown in the closed configuration.
Figure 6:
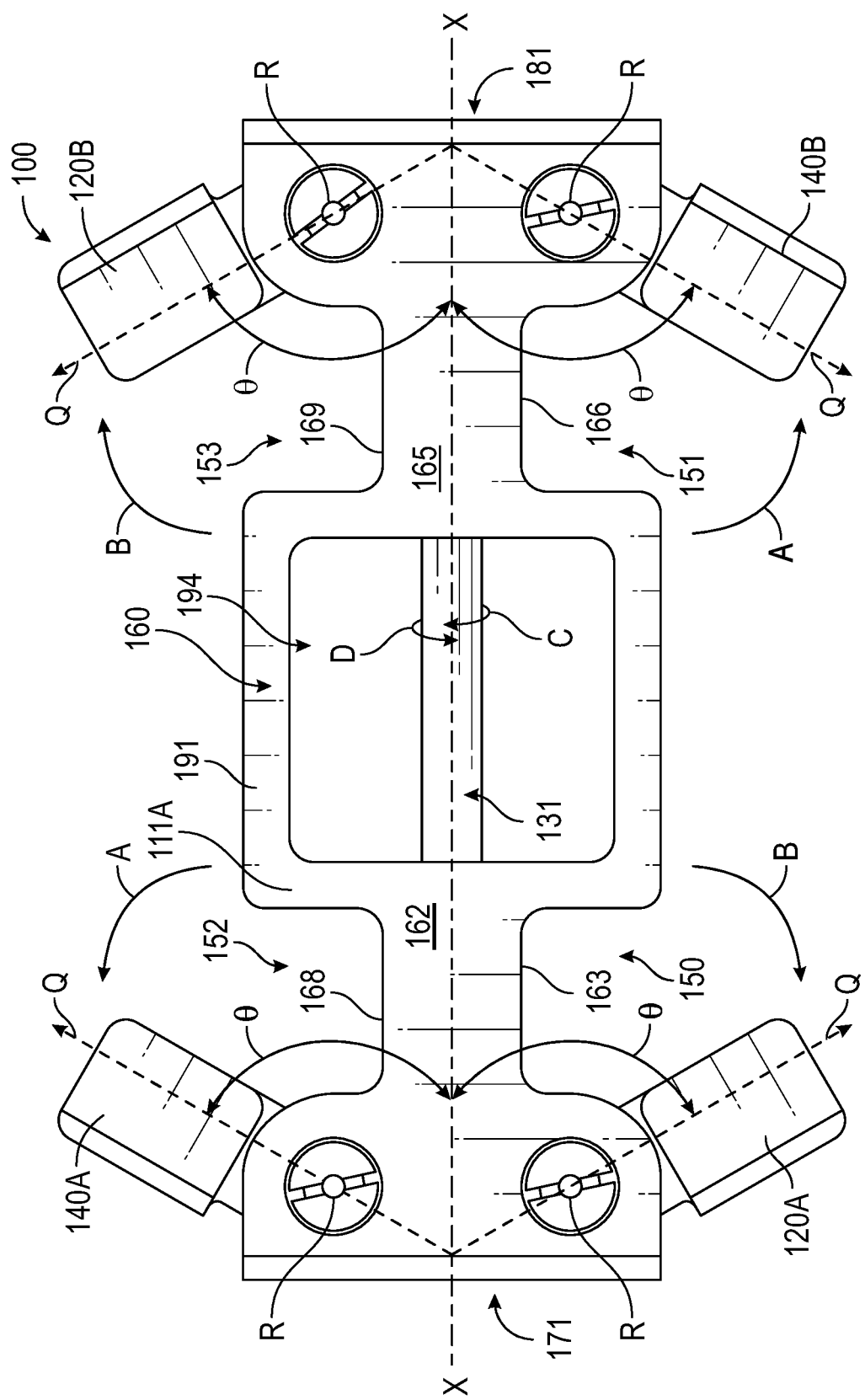
FIG. 6 is a top plan view of the expandable interbody cage device of FIG. 3 shown in an open configuration.
Figure 7:
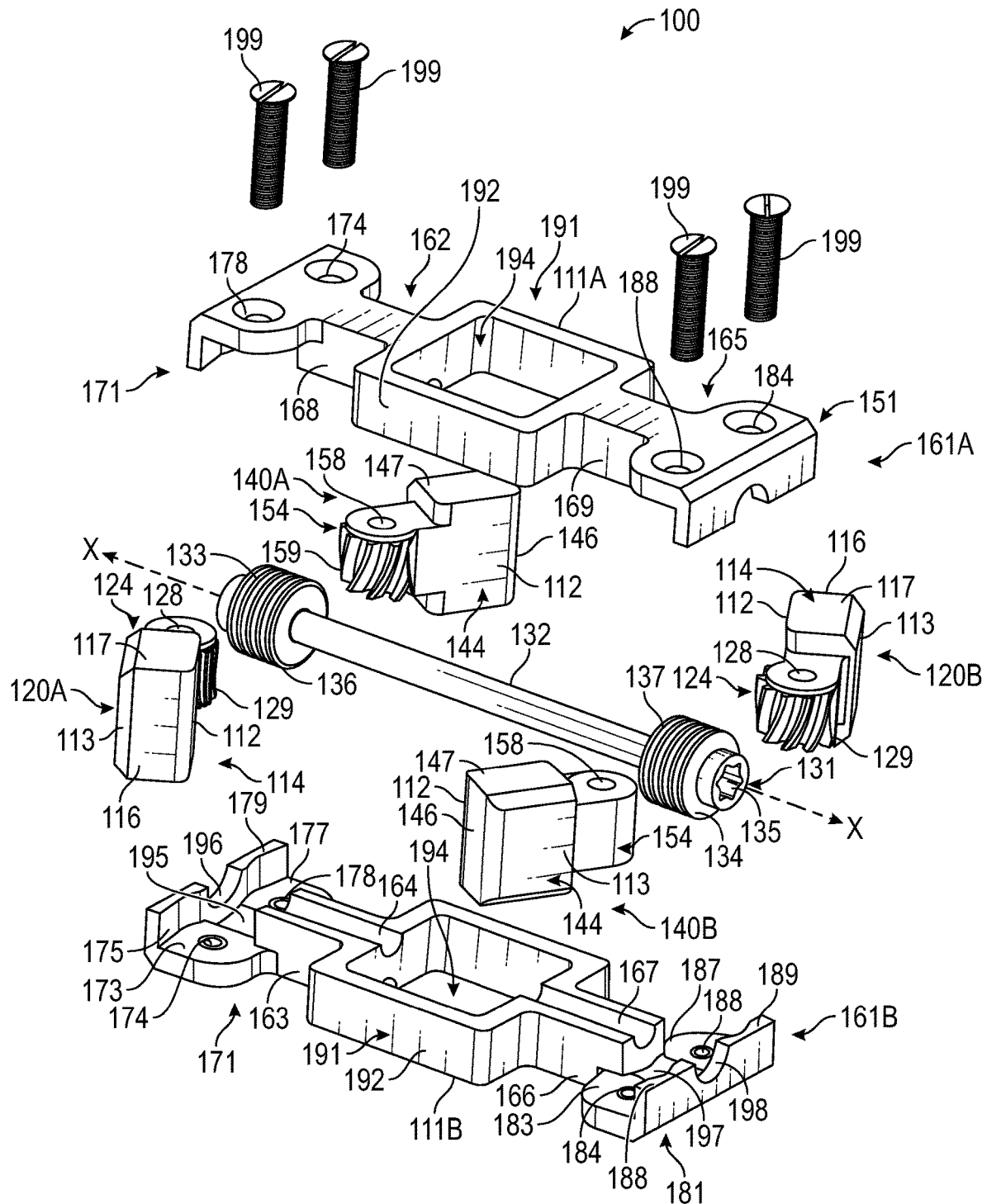
FIG. 7 is an exploded view of the expandable interbody cage device of FIG. 3.
Figure 8:
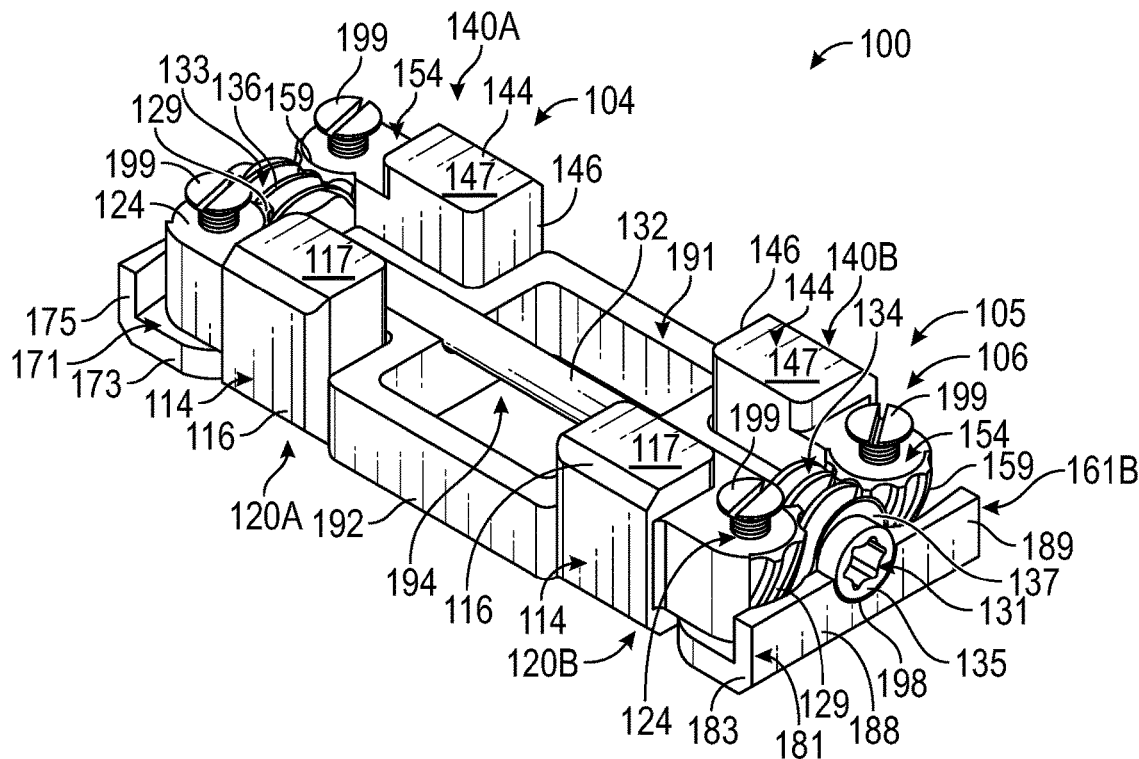
FIG. 8 is a perspective view of the expandable interbody cage device of FIG. 3 shown in a closed configuration with the first cover removed for visibility of internal components of the expandable interbody cage device.
Figure 9:
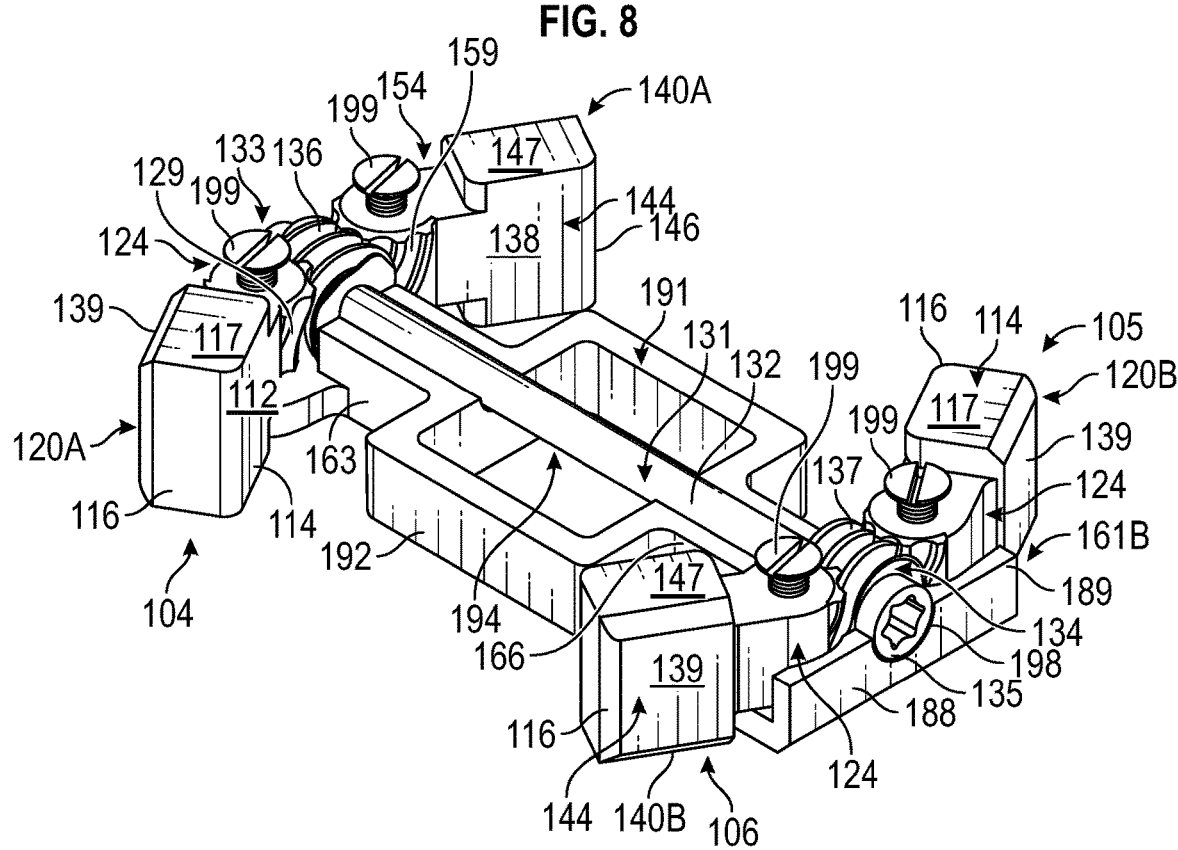
FIG. 9 is a perspective view of the expandable interbody cage device of FIG. 3 shown in an open configuration with the first cover removed for visibility of internal components of the expandable interbody cage device.

FIGS. 3-12 illustrate a first embodiment of the expandable interbody cage device 100. In particular, the expandable interbody cage device 100 includes a cage assembly 160 that defines a first outer planar surface 111A and an opposite second outer planar surface 111B for engaging the endplate of the vertebra. In a preferred embodiment, the cage assembly 160 and plurality of arms 105 attached to the cage assembly 160 are load-bearing such that the expandable interbody cage device 100 can withstand the force of being positioned between two adjacent vertebrae. The expandable interbody cage device 100 also includes an axle 131 encapsulated by the cage assembly 160 that enables a practitioner to manually "open" the expandable interbody cage 100 and rotate a plurality of arms 105 including first, second, third and fourth arms 120A, 140B, 140A and 120B outwardly from a direction of elongation of the axle 131 as illustrated in FIGS. 4, 6 and 9. While in a "closed" position, shown in FIGS. 3, 5 and 8, the plurality of arms 105 are disposed within the cage assembly 160 to provide a small profile for ease of insertion between adjacent vertebrae. The axle 131 includes a first axle head 133 defining a first worm threading 136 and an opposite second axle head 134 defining a second worm threading 137 that are each configured to rotate a respective arm pairing 104 and 106 about respective pivot screw 199 in a clockwise or counterclockwise direction A or B when the axle 131 is rotated in a clockwise or counterclockwise direction C or D. In some embodiments, the expandable interbody cage device 100 includes a bone graft material receptacle 191 configured for receiving a bone graft material.

Figure 11:
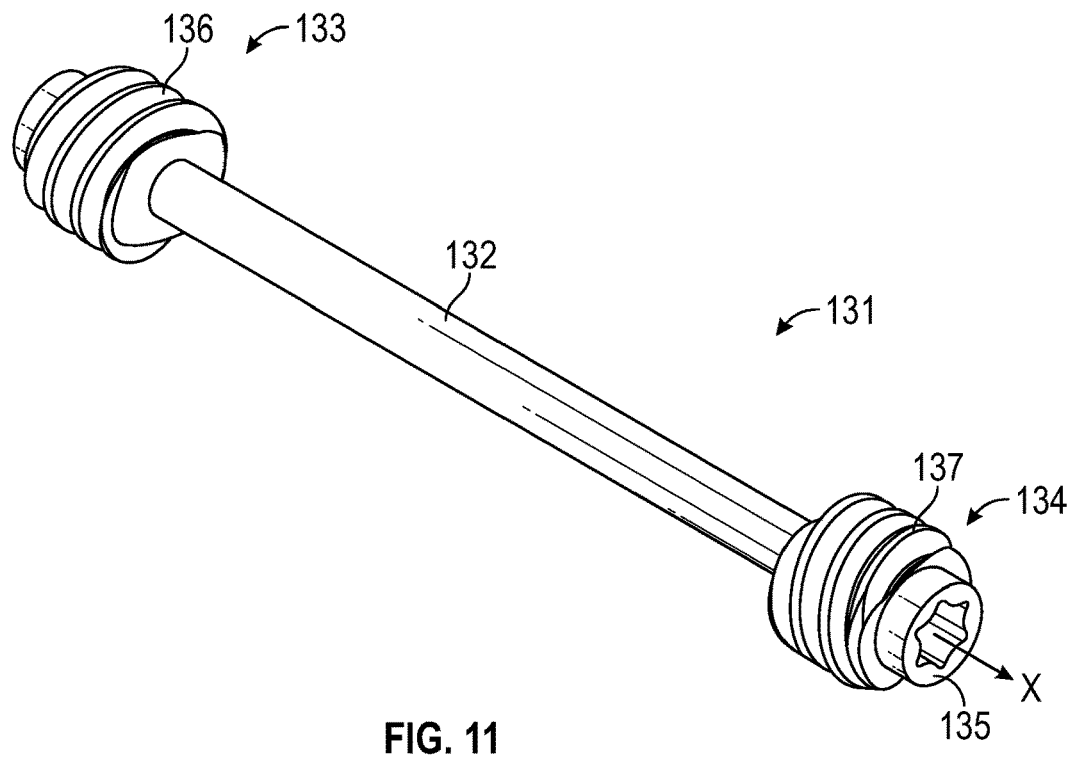
FIG. 11 is a perspective view of an axle for the expandable interbody cage device of FIG. 3 defining a shaft, a first axle head including a first worm gear, and an opposite second axle head including a second worm gear.

Referring directly to FIGS. 8, 9, and 11, the axle 131 rotates each of the arms 120A/120B/140A/140B in a clockwise or counterclockwise direction A or B about their respective pivot screws 199 of the expandable interbody cage device 100. In particular, the axle 131 defines a shaft portion 132 having a first axle head 133 defining the first worm thread 136 and a second axle head 134 defining an opposing second worm thread 137. The first worm thread 136 is threaded in an opposite direction as the opposing second worm thread 137. The first and second axle heads 133 and 134 are each engaged with a respective arm pairing 104 and 106 to actuate each respective arm 120A/120B/140A/140B between the closed configuration of FIG. 8 and the open configuration of FIG. 9. In particular, the first axle head 133 is associated with the first arm pairing 104 which includes a first arm 120A and a third arm 140A. As will be discussed in greater detail below, the first arm 120A and the third arm 140A can have opposing thread directions for engagement with the first axle head 133. When coupled with the first axle head 133, the first arm 120A is lateral to the first axle head 133 on a first side of the axle 131, and the third arm 140A is lateral to the first axle head 133 on a second side of the axle 131, as illustrated. Similarly, the second axle head 134 is associated with the second arm pairing 106 which includes a second arm 140B and a fourth arm 120B. As will be discussed in greater detail below, the second arm 140B and the fourth arm 120B can have opposing thread directions for engagement with the second axle head 134. When coupled with the second axle head 134, the fourth arm 120B is lateral to the second axle head 134 on the second side of the axle 131, and the second arm 140B is lateral to the second axle head 134 on the first side of the axle 131, as illustrated. In some embodiments, the axle 131 includes at least one drive point 135 for engagement with a driving tool (not shown) that enables manual or machine-driven rotation of the axle 131 in the clockwise or counterclockwise rotational direction C or D. As shown, the axle 131 defines a direction of elongation X.

Figure 10A:
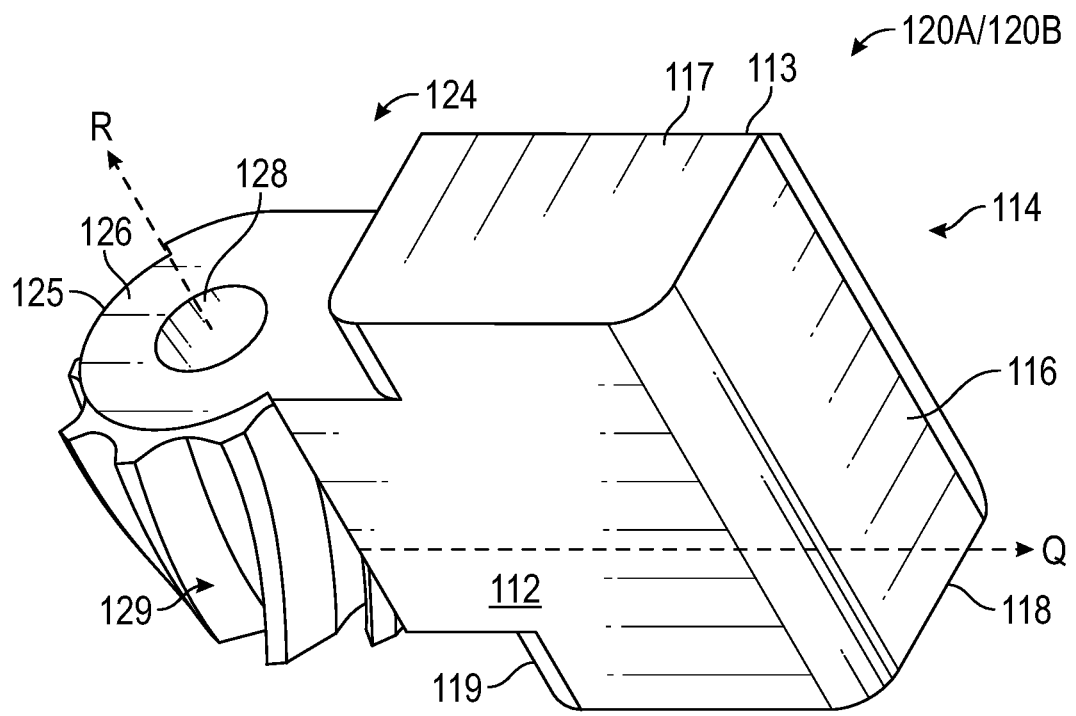
FIGS. 10A and 10B are perspective views of an arm for the expandable interbody cage device of FIG. 3 defining a member portion and a joint portion.
Figure 10B:
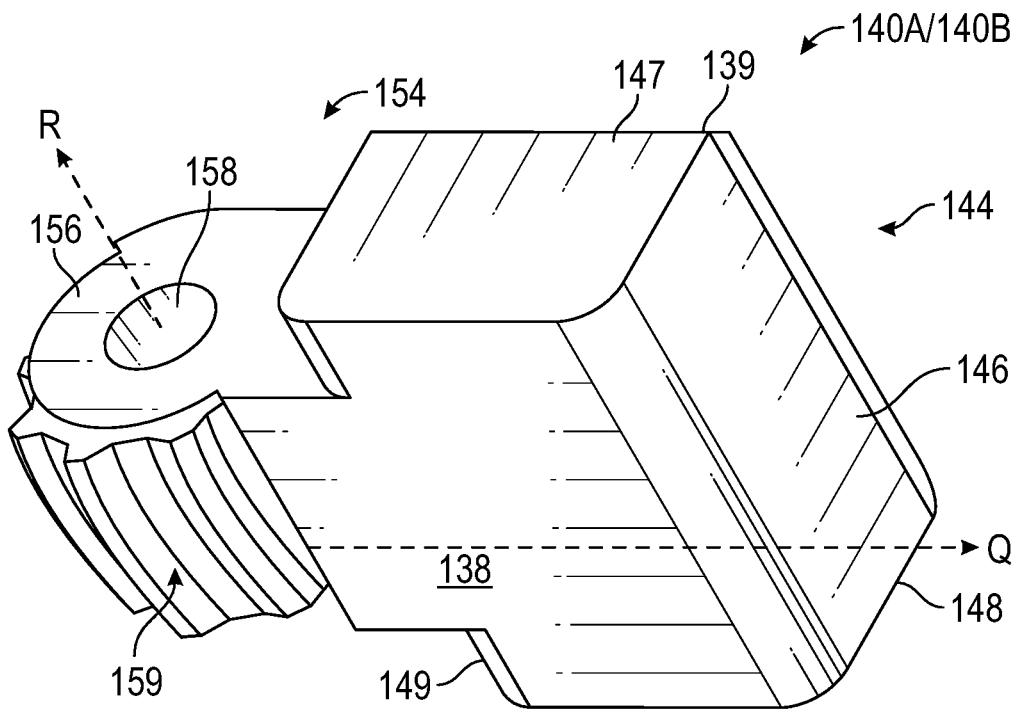

Referring directly to FIGS. 8-10B, each of the arms 120A and 120B of the expandable interbody cage device 100 define a member portion 114 and a joint portion 124. The first arm pairing 104 includes the first arm 120A and the third arm 140A (as will be discussed in greater detail below). Similarly, the second arm pairing 106 includes the second arm 140B and the fourth arm 120B. As shown, the member portion 114 of each arm 120A and 120B defines a distal end 116 that follows a first direction of elongation Q. Each joint portion 124 is configured for engagement with the first axle head 133 or the second axle head 134 of axle 131 and is also configured for placement within the cage assembly 160. In addition, each joint portion 124 includes a curved outer surface 125 defining a plurality of teeth 129 configured for engagement with the worm gear threading 136 or 137 of axle 131. In the embodiment shown, the worm gear threading 136 of the first head 133 of axle 131 associated with the first pair of arms 104 is angled in a first direction, as shown in FIG. 10A. In contrast, as shown in FIG. 10B, the worm gear threading 137 of the second head 134 of axle 131 associated with the second pair of arms 106 is angled in a second direction. In addition, the joint portion 124 of each arm 120A and 120B includes an arm pivot channel 128 that extends along a second direction of elongation R that is perpendicular to the first direction of elongation Q. When the joint portion 124 is coupled to the cage assembly 160, the arm pivot channel 128 aligns with a pivot channel 174 or 188 (FIG. 7) of the cage assembly 160. As shown, the expandable interbody cage device 100 includes a plurality of pivot screws 199 that each secure the arms 120A and 120B to the cage assembly 160 while still enabling rotation of each arm 120A and 120B about the respective pivot screw 199 in the first or opposite second clockwise or counterclockwise directions A and B.

As discussed above, the member portion 114 of each arm 120A and 120B follows the first direction of elongation Q and defines a distal end 116, a first planar surface 117, and an opposite second planar surface 118 as shown in FIG. 10A. The first planar surface 117 and the opposite second planar surface 118 associated with each arm 120A and 120B align with respective outer planar surfaces 111A and 111B of the cage assembly 160 to engage the endplate. As further illustrated, in some embodiments, the member portion 114 of each arm 120A and 120B defines an inner planar surface 112 and an opposite external planar surface 113. When in the closed configuration, the inner planar surfaces 112 of the first and fourth arms 120A and 120B are positioned within respective left and right voids 150 and 152 of the cage assembly 160 with the direction of elongation Q of each member portion 114 being positioned parallel with the direction of elongation X of the axle 131. In the closed configuration, each opposite external planar surface 113 of each arm 120A and 120B aligns with the outer surface 192 of the cage body 191.

Similarly, the member portion 144 of each arm 140A and 140B defines a distal end 146 that follows a first direction of elongation Q. The joint portion 154 of the arms 140A and 140B may be configured for engagement with the first axle head 133 or the second axle head 134 of axle 131 and is also configured for placement within the cage assembly 160. Each joint portion 154 includes a curved outer surface 155 defining a plurality of teeth 159 for engagement with the worm gear threading 136 or 137 of axle 131. In the embodiment shown, the worm gear threading 136 of the first head 133 of axle 131 associated with the first pair of arms 104 is angled in a first direction, as shown in FIG. 10A. In contrast, as shown in FIG. 10B, the worm gear threading 137 of the second head 134 of the axle 131 associated with the second pair of arms 106 is angled in a second direction. In addition, the joint portion 154 of each arm 140A and 140B includes an arm pivot channel 158 that extends along a second direction of elongation R that is perpendicular to the first direction of elongation Q. When the joint portion 154 is coupled to the cage assembly 160, the arm pivot channel 158 aligns with a pivot channel 178 or 184 (FIG. 7) of the cage assembly 160. As shown, the expandable interbody cage device 100 includes a plurality of pivot screws 199 that each secure a respective arm 140A and 140B to the cage assembly 160 while still enabling rotation of each arm 140A and 140B about a respective pivot screw 199 in the first or opposite second clockwise or counterclockwise directions A and B.

As discussed above, each member portion 144 of the second and fourth arms 140A and 140B follows the first direction of elongation Q and defines a distal end 146, a first planar surface 147, and an opposite second planar surface 148 as shown in FIG. 10B. The first planar surface 147 and opposite second planar surface 148 of each arm 140A and 140B align with the outer planar surfaces 111A and 111B of the cage assembly 160 to engage the endplate. As further illustrated, in some embodiments, the member portion 144 of each arm includes an inner planar surface 138 and an opposite external planar surface 139. When in the closed configuration, the inner planar surface 138 of the second and third arms 140B and 140A are positioned within a respective left and right void 151 and 153 of the cage assembly 160 with the direction of elongation Q of the member portion 144 being positioned parallel with the direction of elongation X of the axle 131. In the closed configuration, the opposite external planar surface 113 of each arm 140A and 140B aligns with the outer surface 192 of the cage body 191.

Referring to FIGS. 5-9, when the expandable interbody cage device 100 is in the open configuration, a direction of elongation Q of each arm 120A/120B/140A/140B forms a nonzero angle 8 relative to the direction of elongation X of the axle 131. In particular, to transition from the closed configuration to the open configuration, the axle 131 is operable for manual or machine-driven rotation about the direction of elongation X in the clockwise or counterclockwise direction C or D. Rotation of the axle 131 and associated worm gear threads 136 and 137 of the axle causes each arm 120A/120B/140A/140B to pivot about their respective pivot screws 199 such that the respective distal portion 116/146 of each respective arm 120A/120B/140A/140B is directed away from the axle 131. The continuous nature of the worm threading associated with the axle 131 and each respective arm 120A/120B/140A/140B enables each arm 120A/120B/140A/140B to be positioned at an angle θ that is variable between 0 to 90 degrees relative to the direction of elongation 131 to accommodate differences in anatomy.

In some embodiments, the cage assembly 160 can be manufactured in at least two parts. In the embodiment of FIG. 7, the cage assembly 160 includes a first cage portion 161A and an opposite second cage portion 161B that collectively form the cage assembly 160 when coupled together. The first and second cage portions 161A and 161B collectively encapsulate the axle 131. Each cage portion 161A and 161B includes a first cage head 171 and an opposite second cage head 181 which are each respectively configured to receive the first axle head 133 and the second axle head 134 of axle 131. The first and second cage heads 171 and 181 each engage the respective first arm pairing 104 and second arm pairing 106, as shown in FIGS. 7-9. Assembly of the expandable interbody cage device 100 is illustrated in terms of the second cage portion 161B and the first cage portion 161A being oriented facedown and coupled with the second cage portion 161B to encapsulate the axle 131 and the respective joint portions 124/154 of each arm 120A/120B/140A/140B.

Figure 12:
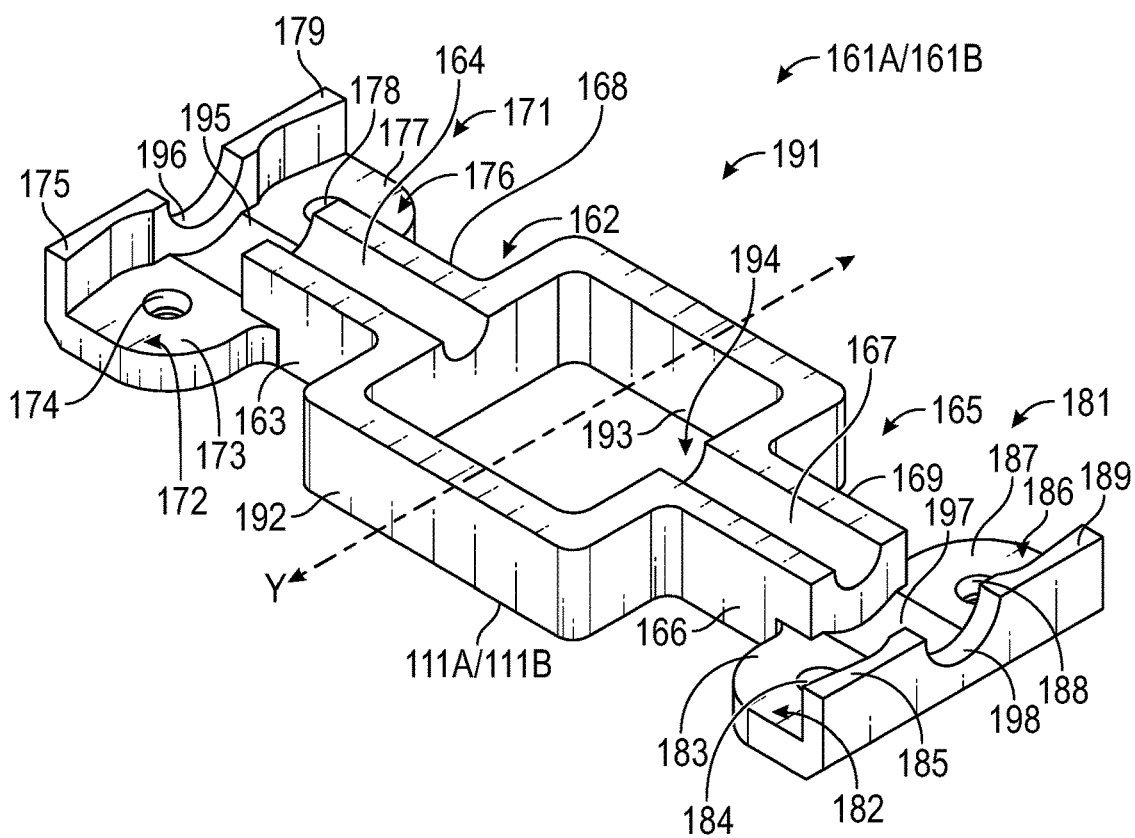
FIG. 12 is a perspective view of a first or second cage portion of the expandable interbody cage device of FIG. 3 defining a cover body including an axle channel, a first head and an opposite second head, and one or more graft material receptacles.
Figure 13:
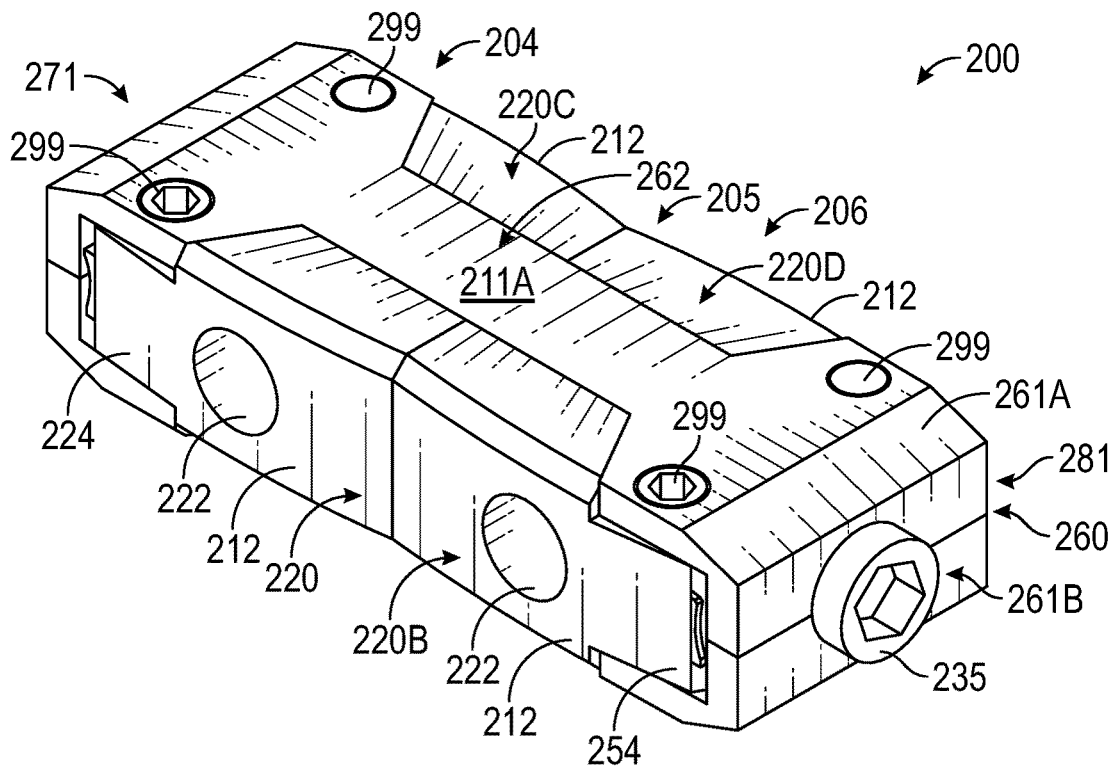
FIG. 13 is a perspective view of a second embodiment of the expandable interbody cage device of FIGS. 2A and 2B shown in a closed configuration.

As shown in FIGS. 8, 9 and 12, the first cage head 171 of the cage assembly 160 defines a left shoulder 172 and an opposite right shoulder 176 that are each directly adjacent to a central seat 195. The left shoulder 172 is configured to receive the first arm 120A of the first pair of arms 104, and the right shoulder 176 is also configured to receive a second arm 140A of the first pair of arms 104. As shown, the left shoulder 172 defines an inner surface 173 and a shoulder pivot channel 174 is defined through the inner surface 173 to communicate with an outer planar surface 111 of each cage portion 161A/161B. The inner surface 173 and the shoulder pivot channel 174 are collectively configured to engage the joint portion 124 of the first arm 120A. The left shoulder 172 further defines a left lip 175 having a direction of elongation that is perpendicular to the inner surface 173 of the left shoulder 172. The central seat 195 defines a depression within the first head 171 and is configured to receive a first axle head 133 of the axle 131. A central notch 196 is located adjacent to the first lip 175 and in association with the central seat 195 for allowing access to the axle 131 to enable manual or powered rotation of the axle 131 when seated within each respective cage portion 161A/161B. As further shown, the right shoulder 176 also defines an inner surface 177 and a shoulder pivot channel 178 defined through the inner surface 177 to communicate with an outer planar surface 111 of the cage portions 161A/161B. The inner surface 177 and the shoulder pivot channel 178 collectively engage a joint portion 154 of the second arm 140. The right shoulder 176 further defines a right lip 175 having a direction of elongation that is perpendicular to the inner surface 177 of the right shoulder 172. As shown, the components of the left shoulder 172 and the right shoulder 176 are mirrored about the central seat 195.

Similarly, the second cage head 181 of each cage portion 161A/161B defines a left shoulder 182 and an opposite right shoulder 186 that are each directly adjacent to a central seat 197. As shown, the second cage head 181 is mirrored about an axis Y (FIG. 12). The left shoulder 182 is configured to receive a second arm 140B of a second pair of arms 106, and the right shoulder 186 is configured to receive a first arm 120A of the second pair of arms 106. It should be noted that the positions of the first and fourth arms 120A/120B of the first pair of arms 104 and the fourth and second arms 140A/140B of the second pair of arms 106 are swapped between the first cage head 171 and the second cage head 181 of the cage assembly 160 to accommodate a reversed thread angle between the first axle head 133 and the second axle head 134.

As shown, the left shoulder 182 defines an inner surface 183 and a shoulder pivot channel 184 defined through the inner surface 183 to communicate with each outer planar surface 111A/111B. The inner surface 183 and the shoulder pivot channel 184 are collectively configured to engage a joint portion 154 of the second arm 140B of the second pair of arms 106. The left shoulder 182 further defines a left lip 185 having a direction of elongation that is perpendicular to the inner surface 183 of the left shoulder 182. The central seat 197 defines a depression within the first head 181 and is configured to receive the second axle head 134 of the axle 131. A central notch 198 is located adjacent to the first lip 185 and in association with the central seat 197 and enables access to the axle 131 to allow manual or powered rotation of the axle 131 when the axle 131 is seated within each cage portion 161A/161B. As further shown, the right shoulder 186 also defines an inner surface 187 and a shoulder pivot channel 188 is defined through the inner surface 187 to communicate with outer planar surfaces 111A/111B. The inner surface 187 and the shoulder pivot channel 188 are collectively configured to engage a joint portion 124 of the first arm 120A. The right shoulder 186 further defines a right lip 185 having a direction of elongation that is perpendicular to the inner surface 187 of the right shoulder 182. As shown, the components of the left shoulder 182 and the right shoulder 186 are mirrored about the central seat 197.

Each cage portion 161A/161B further includes at least a first neck portion 162 defining an axle channel 164 defined axially along a direction of elongation of the respective cage portion 161A/161B for receipt of the shaft 132 of axle 131. In some embodiments, a left exterior surface 163 of the first neck portion 162 defines a left void 150 for receipt of the inner planar surface 112 of member portion 114 of the first arm 120A, and a right exterior surface 168 of the first neck portion 162 defines a right void 152 for receipt of the inner planar surface 138 of the member portion 144 of the second arm 140A. Further, in the embodiment of FIG. 12, each cage portion 161A/161B further includes a second neck portion 165 in association with the second head 181 and defines an axle channel 167 along a direction of elongation of the respective cage portion 161A/161B for receipt of a shaft 132 of axle 131. In some embodiments, a left exterior surface 166 of the second neck portion 165 defines a left void 151 for receipt of the inner planar surface 138 of the member portion 144 for the second arm 140B, while a right exterior surface 168 of the second neck portion 165 defines a right void 153 for receipt of the inner planar surface 112 of the member portion 114 for the first arm 120B.

In the embodiment of FIGS. 3-12, the first neck portion 162 and the second neck portion 165 are mirrored and separated from one another by a cage body 191 that includes at least one cavity 194 for receipt of bone graft material that aids in fusion of the vertebrae. The cage body 191 defines an outer surface 192 and an interior surface 193. As shown in FIGS. 3 and 8, when in the closed configuration, the outer surface 192 of the cage body 191 aligns with the external planar surface 113 of the member portions 114 and 154 of each respective arm 120A/120B/140A/140B. In some embodiments, the axle 131 bisects the cavity 194. The cavity 194 can also be packed with bone graft material (not shown) to encourage bone growth and fusion of the vertebrae.

Figure 14:
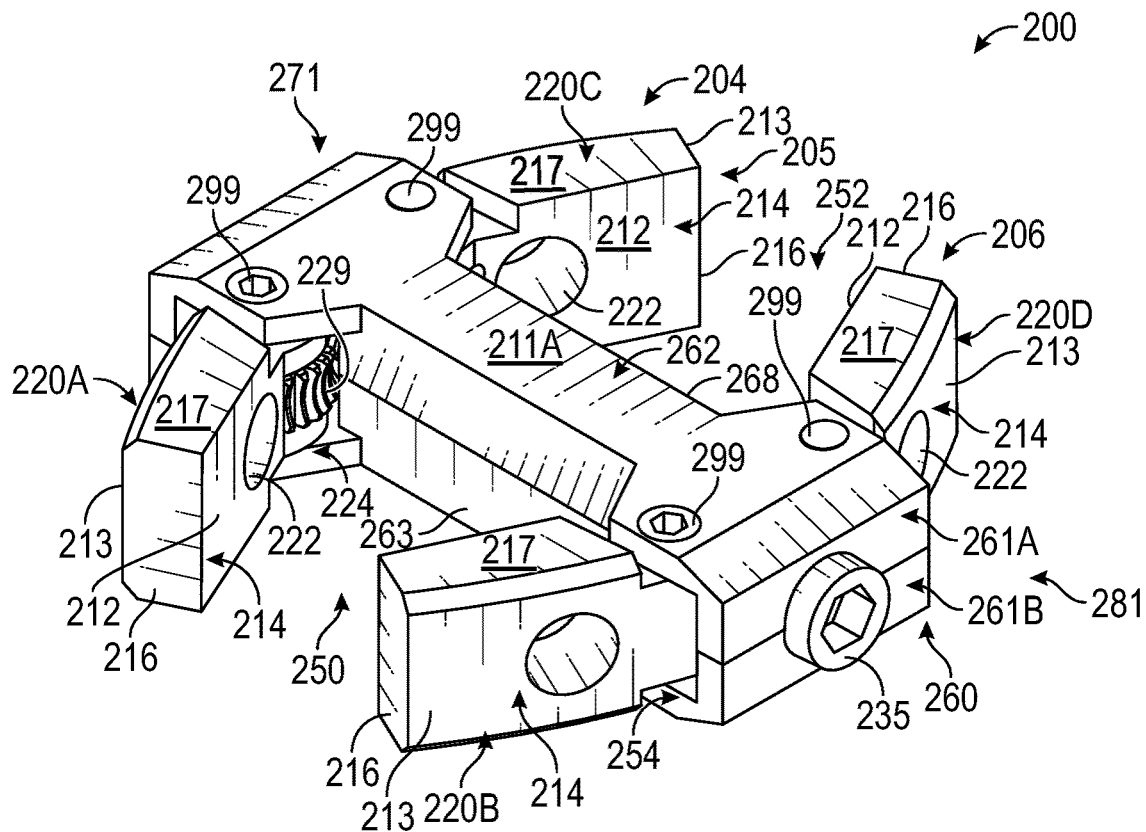
FIG. 14 is a perspective view of the expandable interbody cage device of FIG. 13 shown in an open configuration.
Figure 15:
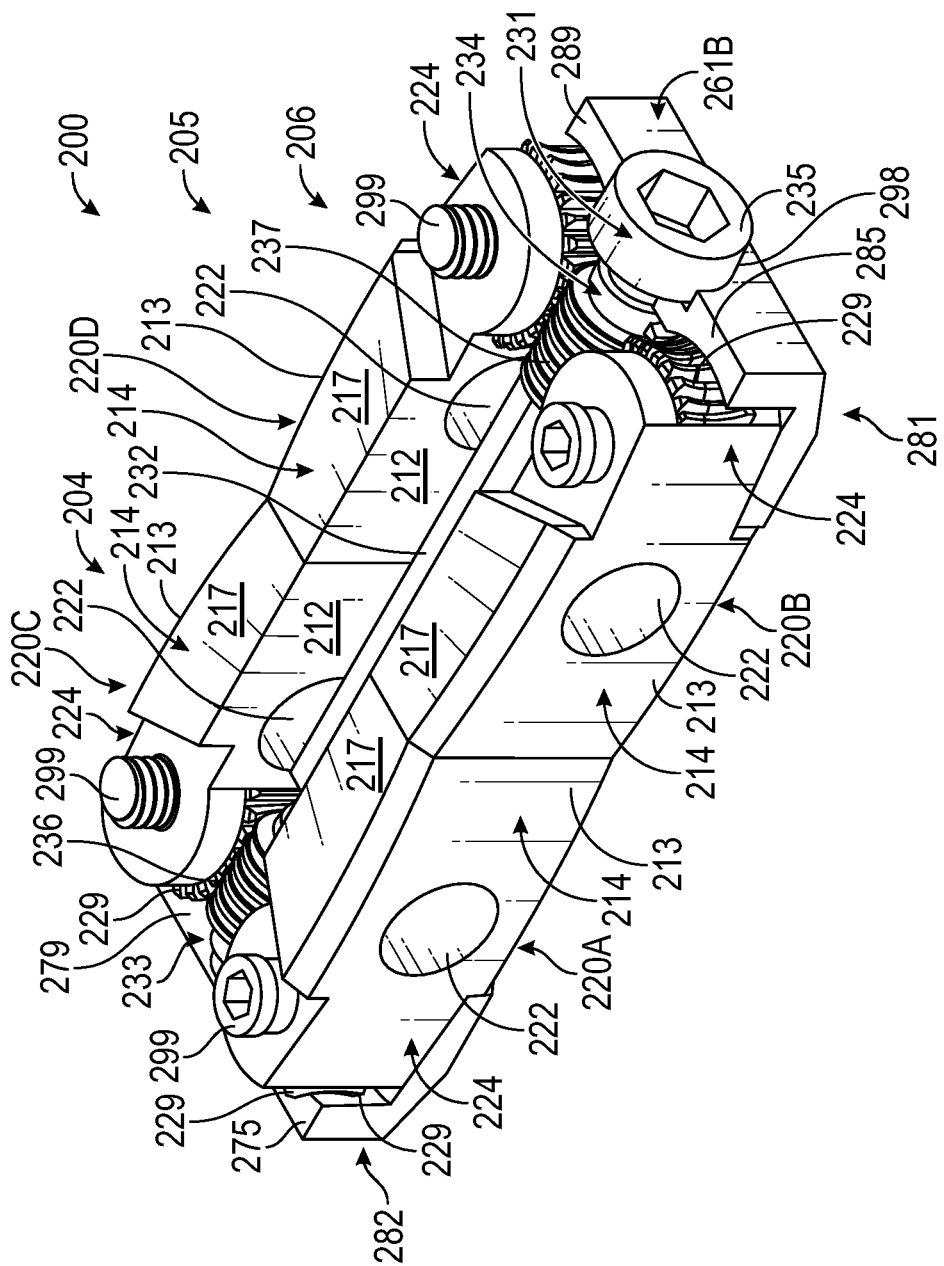
FIG. 15 is a perspective view of the expandable interbody cage device of FIG. 13 shown in a closed configuration with the first cover removed for visibility of internal components of the expandable interbody cage device.
Figure 16:
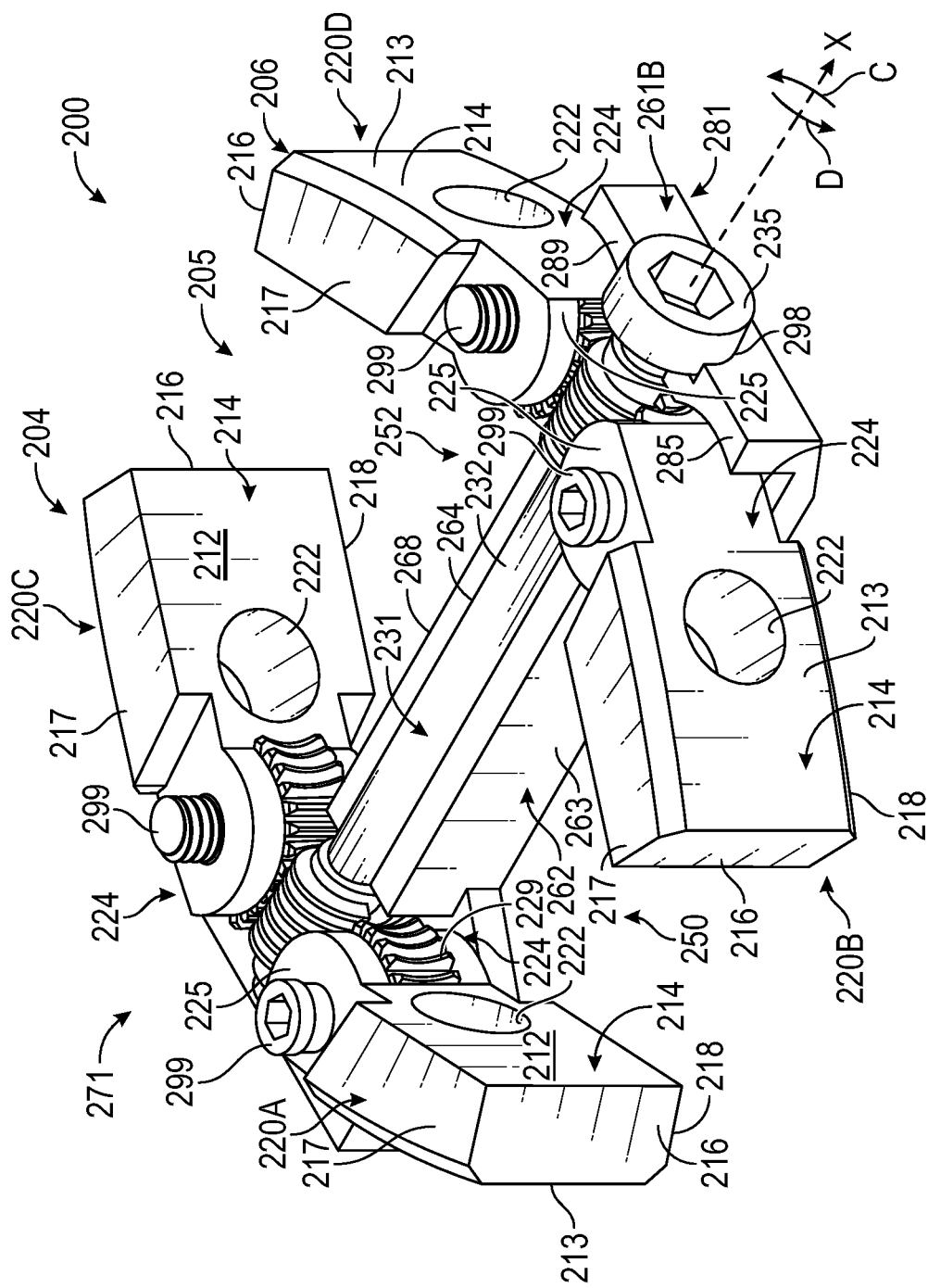
FIG. 16 is a perspective view of the expandable interbody cage device of FIG. 13 shown in an open configuration of the expandable interbody cage device with the first cover removed for visibility of internal components of the expandable interbody cage device.

FIGS. 13-18B illustrate a second embodiment of the expandable interbody cage device, designated 200. In particular, the expandable interbody cage device 200 includes a cage assembly 260 that defines a first outer planar surface 211A and an opposite second outer planar surface 211B for engaging the endplate of the vertebra. In a preferred embodiment, the cage assembly 260 is load-bearing such that the expandable interbody cage device 200 can withstand the force of being positioned between two adjacent vertebrae. The expandable interbody cage device 200 also includes an axle 231 encapsulated by the cage assembly 260 that enables a practitioner to "open" the expandable interbody cage 200 and rotate a plurality of arms 205 outwardly along a direction of elongation of the cage assembly 260 as illustrated in FIGS. 14 and 16. While in a "closed" position shown in FIGS. 13 and 15, the arms 205 are tucked into the cage assembly 260 to provide a slim profile for ease of insertion between vertebrae. The axle 231 includes a first axle head 233 defining a first worm threading 236 and an opposite second axle head 234 defining a second worm threading 237 that are each configured to rotate a respective pair of arms 204 and 206 about a respective pivot screw 299 in a clockwise or counterclockwise direction A or B when the axle 231 is rotated in a clockwise or counterclockwise direction C or D. In some embodiments, the expandable interbody cage device 200 includes a plurality of bone graft ports 222, each associated with a respective arm 220A/220B/220C/220D for packing bone graft material into the opened expandable interbody cage device 200.

Figure 17:
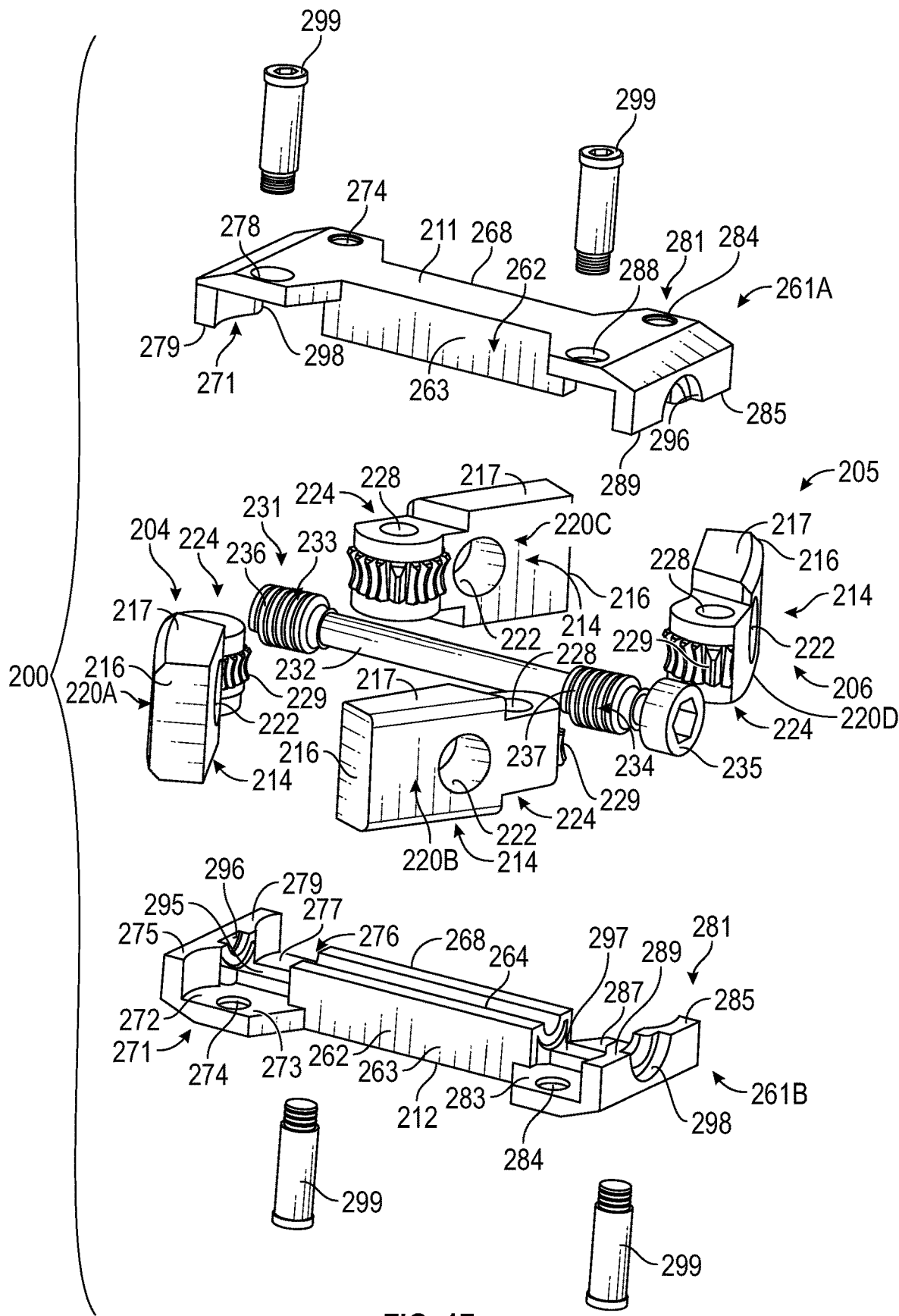
FIG. 17 is an exploded view of the expandable interbody cage device of FIG. 13.
Figure 18A:
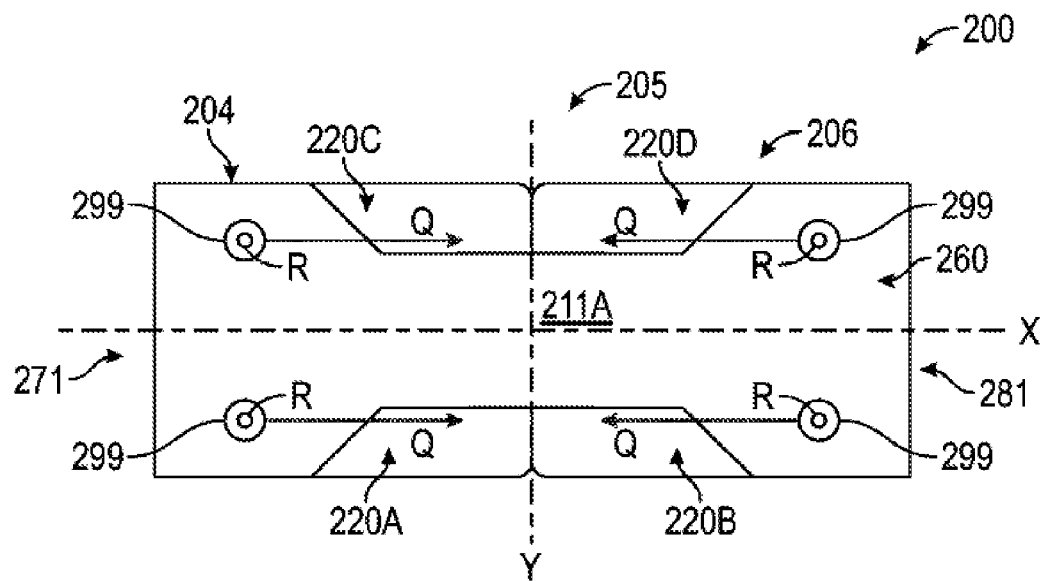
FIGS. 18A and 18B are a series of illustrations showing a top plan view of the expandable interbody cage device of FIG. 13 in the closed configuration and in the open configuration.
Figure 18B:
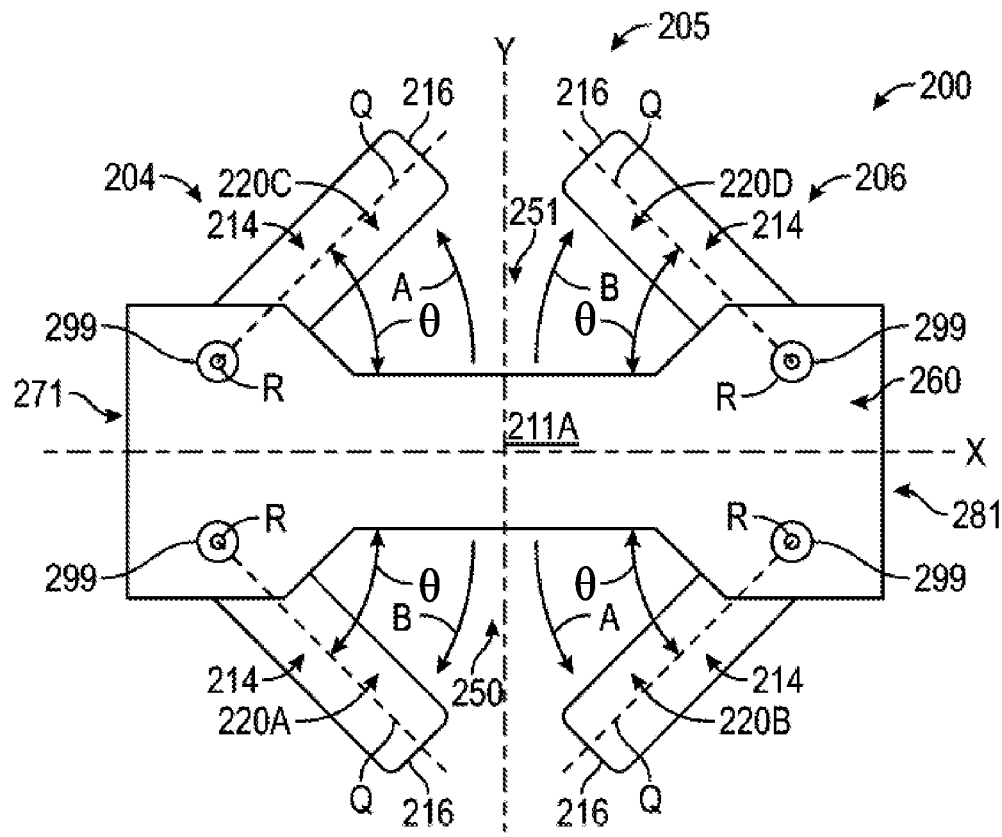
Figure 20:
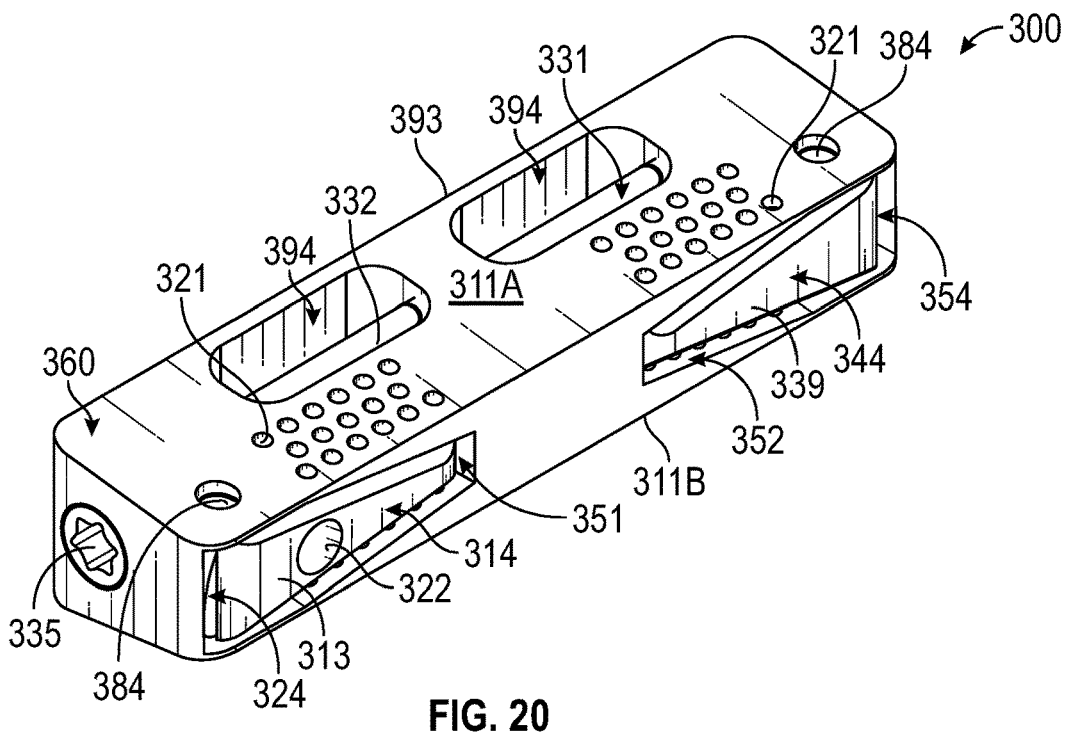
FIG. 20 is a perspective view of the expandable interbody cage device of FIG. 19 shown in the closed configuration.

Referring directly to FIGS. 15, 16 and 17, the axle 231 rotates each respective arm 220A/220B/220C/220D in a clockwise or counterclockwise direction A or B about a respective pivot screw 299. In some embodiments, the axle 231 defines a shaft portion 232 having a first axle head 233 forming a first worm thread 236 and a second axle head 234 forming an opposing second worm thread 237. The first worm thread 236 is threaded in an opposite direction as the opposing second worm thread. In some embodiments, the first and second axle heads 233 and 234 are each engaged with a respective arm pairing 204 and 206 to actuate each arm 220 between the closed configuration of FIG. 15 and the open configuration of FIG. 16.

In the embodiment shown, the worm gear threading 236 of the first head 233 of axle 231 associated with the first pair of arms 204 is angled in a first direction, and the worm gear threading 237 of the second head 234 of axle 231 associated with the second pair of arms 206 is angled in a second direction. In particular, the first axle head 233 is associated with the first arm pairing 204 which includes a first arm 220A and a third arm 220C. In contrast with the first arm 120A and the third arm 140A of the first arm pairing 104 in the first embodiment (FIG. 7), which differ by having teeth 129 angled in opposing directions for engagement with the first axle head 133, the first arm 220A and the third arm 220C of the first arm pairing 204, include teeth 229 that are not angled, and can therefore be manufactured as two of the same component. When coupled with the first axle head 233, the first arm 220A is lateral to the first axle head 233 on a left side of the axle 231, and the third arm 220C is lateral to the first axle head 233 on a right side of the axle 231.

Similarly, the second axle head 234 is associated with the second arm pairing 206 which includes a second arm 220B and a fourth arm 220D. In contrast with the second arm 140B and the fourth arm 120B of the second arm pairing 106 of the first embodiment shown in FIG. 7, the second arm 220B and the fourth arm 220D of the second arm pairing 206 include teeth 229 that are not angled and can therefore be manufactured as two of the same component. When coupled with the second axle head 234, the second arm 220B is lateral to the second axle head 234 on the left side of the axle 231, and the fourth arm 220D is lateral to the second axle head 234 on the right side of the axle 231. In some embodiments, the axle 231 includes at least one drive point 235 for engagement with a driving tool (not shown) that enables manual or machine-driven rotation of the axle 231 in a clockwise or counterclockwise direction C or D. As shown, the axle 231 defines a direction of elongation X.

In continued reference to FIGS. 15-18B, each arm 220A/220B/220C/220D of the expandable interbody cage device 200 defines a member portion 214 and a joint portion 224. The first pair of arms 204 of the plurality of arms 205 includes a first arm 220A and a second arm 220B associated with the first axle head 233. Similarly, the second pair of arms 206 of the plurality of arms 205 includes the third arm 220C and the fourth arm 220D associated with the second axle head 234. The member portion 214 of each arm 220A/220B/220C/220D defines a distal end 216 that follows a first direction of elongation Q. The joint portion 224 of each arm 220A/220B/220C/220D is configured for engagement with the first axle head 233 or the second axle head 234 of the axle 231 and is also configured for placement within the cage assembly 260. The joint portion 224 includes a curved outer surface 225 defining a plurality of teeth 229 for engagement with the worm gear threading 236 or 237 of axle 231. As shown, the joint portion 224 of each arm 220A/220B/220C/220D includes an arm pivot channel 228 that extends along a second direction of elongation R that is perpendicular to the first direction of elongation Q. When each joint portion 224 is coupled to the cage assembly 260, each arm pivot channel 228 aligns with a respective shoulder pivot channel 274/278/284/288 (FIG. 17) of the cage assembly 260. As shown, the expandable interbody cage device 200 includes the plurality of pivot screws 299 that each secures a respective arm 220A/220B/220C/220D to the cage assembly 260 while still enabling rotation of each arm 220A/220B/220C/220D about a respective pivot screw 299 in the clockwise or counterclockwise directions A or B. In some embodiments, each arm 220A/220B/220C/220D can include a bone graft port 222 for insertion of bone graft material for improved fusion of the joint.

As discussed above, the member portion 214 of each arm 220A/220B/220C/220D follows the first direction of elongation Q and defines a distal end 216, a first planar surface 217, and an opposite second planar surface 218 as shown in FIG. 10. The first planar surface 217 and the opposite second planar surface 218 of each arm 220A/220B/220C/220D aligns with the outer planar surfaces 211A and 211B of the cage assembly 260 to engage the endplate. As further illustrated, in some embodiments, the member portion 214 of each arm 220A/220B/220C/220D defines an inner planar surface 212 and an opposite external planar surface 213. When in the closed configuration, the inner planar surface 212 of each respective arm 220A/220B/220C/220D is positioned against an elongated neck portion 262 of the cage assembly 260 with the direction of elongation Q of the member portion 214 being positioned parallel with the direction of elongation X of the axle 231.

Referring to FIGS. 15-18B, when the expandable interbody cage device 200 is in the open configuration, a direction of elongation Q of each arm 220A/220B/220C/220D forms a nonzero angle θ relative to the direction of elongation X of the axle 231. In particular, to transition from the closed configuration to the open configuration, the axle 231 is operable for manual or machine-driven rotation about the direction of elongation X in a clockwise or counterclockwise direction C or D. Rotation of the axle 231 and associated worm gear threads 236 and 237 of the axle 231 causes each arm 220A/220B/220C/220D to pivot about their respective pivot screws 299 such that the distal portion 216 of each respective arm 220A/220B/220C/220D is directed away from the axle 231. The continuous nature of the worm threading associated with the axle 231 and each respective arm 220A/220B/220C/220D enables each arm 220A/220B/220C/220D to be positioned at an angle θ that is variable between 0 to 90 degrees relative to the direction of elongation X of the axle 231 to accommodate differences in anatomy.

In some embodiments, the cage assembly 260 can be manufactured in at least two parts. In the embodiment of FIG. 17, the cage assembly 260 includes a first cage portion 261A and an opposite second cage portion 261B that collectively form the cage assembly 260. The first and second cage portions 261A and 261B collectively encapsulate the axle 231. In addition, each cage portion 261A and 261B includes a first cage head 271 and an opposite second cage head 272 which are each respectively configured to receive the first axle head 233 and the second axle head 234 of axle 231. The first and second cage heads 271 and 272 engage a respective first arm pairing 204 and a second arm pairing 206 as shown in FIGS. 13-17. Referring to FIGS. 15-17, assembly of the expandable interbody cage device 200 is illustrated in terms of the second cage portion 261B and the first cage portion 261A being oriented facedown and coupled with the second cage portion 261B to encapsulate the axle 231 and the joint portions 224 of each arm 222A/222B/222C/222D.

As shown in FIG. 17, each cage portion 261A/261B includes a first cage head 271 defining a left shoulder 272 and an opposite right shoulder 276 that are each formed directly adjacent to a central seat 295. The left shoulder 272 is configured to receive the first arm 220A of the first pair of arms 204, and the right shoulder 276 is configured to receive a second arm 220B of the first pair of arms 204. As shown, the left shoulder 272 defines an inner surface 273, while a shoulder pivot channel 274 being formed through the inner surface 273 to communicate with the outer planar surface 211 of the cage portions 261A/261B. The inner surface 273 and the shoulder pivot channel 274 are collectively configured to engage a joint portion 224 of the first arm 220A of the first pair of arms 204. The left shoulder 272 further defines a left lip 275 having a direction of elongation that is perpendicular to the inner surface 273 of the left shoulder 272. The central seat 295 defines a depression within the first head 271 and is configured to receive a first axle head 233 of axle 231. A central notch 296 is located adjacent to the first lip 275 and in association with the central seat 295 and allows access to the axle 231 to enable manual or powered rotation of the axle 231 when the axle 231 is seated within each cage portion 261A/261B. As further shown, the right shoulder 276 also defines an inner surface 277 and a shoulder pivot channel 278 defined through the inner surface 277 to communicate with an outer planar surface 211 of each cage portion 261A/261B. The inner surface 277 and the shoulder pivot channel 278 collectively engage a joint portion 254 of the second arm 220B. The right shoulder 276 further defines a right lip 275 having a direction of elongation that is perpendicular to the inner surface 277 of the right shoulder 272. As shown, the components of the left shoulder 272 and the right shoulder 276 are mirrored about the central seat 295.

Similarly, the second cage head 281 of each cage portion 261A/261B defines a left shoulder 282 and an opposite right shoulder 286 that are each directly adjacent to a central seat 297. As shown, the second cage head 281 is mirrored about an axis Y. The left shoulder 282 is configured to receive a third arm 220C of the second pair of arms 206, and the right shoulder 286 is configured to receive a fourth arm 220D of the second pair of arms 206.

As shown, the left shoulder 282 defines an inner surface 283 and a shoulder pivot channel 284 defined through the inner surface 283 to communicate with each outer planar surface 211A/211B of cage portions 261A/261B. The inner surface 283 and the shoulder pivot channel 284 are collectively configured to engage a joint portion 254 of the third arm 220C. The left shoulder 282 further defines a left lip 285 having a direction of elongation that is perpendicular to the inner surface 283 of the left shoulder 282. The central seat 297 defines a depression within the first head 281 and is configured to receive a second axle head 234 of axle 231. A central notch 298 is located adjacent to the first lip 285 and is in association with the central seat 297, thereby enabling access to the axle 231 for manual or machine-driven rotation of the axle 231 when seated within each cage portion 261A/261B. As further shown, the right shoulder 286 also defines an inner surface 287 and a shoulder pivot channel 288 defined through the inner surface 287 to communicate with the respective outer planar surface 211A/211B of each cage portion 261A/261B. The inner surface 287 and the shoulder pivot channel 288 are collectively configured to engage a joint portion 224 of the fourth arm 220D. The right shoulder 286 further defines a right lip 285 having a direction of elongation that is perpendicular to the inner surface 287 of the right shoulder 282. As shown, the components of the left shoulder 282 and the right shoulder 286 are mirrored about the central seat 297.

Each cage portion 261A/261B has an elongated neck portion 262 defining an axle channel 264 formed axially along a direction of elongation of each cage portion 261A/261B for receipt of a shaft 232 of axle 231. In some embodiments, the elongated neck portion 262 defines a left exterior surface 263 for receipt of the inner planar surfaces 212 of the member portions 214 for the first and third arms 220A and 220C. In addition, the elongated neck portion 262 defines a right exterior surface 268 for receipt of the inner planar surfaces 212 of the member portions 244 for the second and fourth arms 220B and 220D.

Referring back to the first embodiment of FIGS. 3-12, the first neck portion 162 and the second neck portion 165 are mirrored and are separated from one another by a cage body 191 that includes at least one cavity 194 for receipt of bone graft material that aids in fusion of the vertebrae. The cage body 191 includes an outer surface 192 and an opposite interior surface 193. The cavity 194 can be packed with bone graft material (not shown) to encourage bone growth and fusion of the vertebrae. In contrast, in the second embodiment of FIGS. 14 and 16, the "opened" plurality of arms 205 along the left side including the first and third arms 220A and 220C collectively form a left void 250 for packing bone graft material for improved fusion of the joint. Specifically, a bone graft material can be packed through the bone graft ports 222 of the first and third arms 220A and 220C and into the left void 250 formed by the open first and third arms 220A and 220C. Similarly, the "opened" plurality of arms 205 along the right side including the second and fourth arms 220B and 220D form a right void 252 for packing bone graft material for improved fusion of the joint. Specifically, bone graft material can be packed through the bone graft ports 222 of the second and fourth arms 220B and 220D and into the right void 252 formed by the open second and fourth arms 220B and 220D. This alteration of the embodiment allows each arm 220A/220B/220C/220D to have a longer length and thus the expandable interbody cage device 200 can be expanded to contact a larger surface area of the endplate.

FIGS. 19-26 illustrate a third embodiment of the expandable interbody cage device 300. In particular, the expandable interbody cage device 300 includes a cage assembly 360 that defines a first outer planar surface 311A and an opposite second outer planar surface 311B for engaging the endplate of the vertebra. In a preferred embodiment, the cage assembly 360 is load-bearing such that the expandable interbody cage device 300 can withstand the force of being positioned between two vertebrae. The expandable interbody cage device 300 also includes an axle 331 encapsulated by the cage assembly 360 that enables a practitioner to "open" the expandable interbody cage device 300 and rotate a plurality of arms 305 outwardly from a direction of elongation of the cage assembly 360 as illustrated in FIGS. 19, 21 and 23-25. While in a "closed" position shown in FIGS. 20, 22 and 26, the arms 305 are tucked into the cage assembly 360 as shown to provide a slim profile for ease of insertion between adjacent vertebrae. The axle 331 includes a first axle head 333 defining a first worm threading 336 and an opposite second axle head 334 defining a second worm threading 337 that are each configured to rotate a respective arm 320 and 340 about a respective pivot screw 399 in a clockwise or counterclockwise direction A or B when the axle 331 is rotated in a clockwise or counterclockwise direction C or D. In some embodiments, an arm 320 or 340 of the expandable interbody cage device 300 may include a bone graft port 322 for packing bone graft material into the opened expandable interbody cage device 300.

The axle 331 rotates each arm 320 and 340 in a clockwise or counterclockwise direction A or B about a respective pivot screw 399 of the expandable interbody cage device 300. In particular, the axle 331 defines the shaft portion 332 having a first axle head 333 defining the first worm thread 336 and the second axle head 334 defining an opposing second worm thread 337. The first worm thread 336 is threaded in an opposite direction as the opposing second worm thread 337. The first and second axle heads 333 and 334 each engage a respective arm 330 and 340 to actuate each arm 320 and 340 between the closed configuration of FIG. 20 and the open configuration of FIG. 19.

In the embodiment shown, the worm gear threading 336 of the first head 333 for axle 331 associated with the first arm 320 is angled in a first direction, as shown in FIG. 10A. In contrast, as shown in FIG. 10B, the worm gear threading 337 of the second head 334 for axle 331 associated with the second arm 340 is angled in a second direction. As illustrated, when coupled with the first axle head 333, the first arm 320 is lateral to the first axle head 333, and the second arm 340 is lateral to the second axle head 334. In some embodiments, the axle 331 includes at least one drive point 335 for engagement with a driving tool (not shown) that enables manual or machine-driven rotation of the axle 331 in the clockwise or counterclockwise direction C or D. As shown, the axle 331 defines a direction of elongation X.

In reference to FIGS. 19-24, each arm 320/340 of the expandable interbody cage device 300 is illustrated defining a member portion 314 and a joint portion 324. The first arm 320 is associated with the first axle head 333 and the second arm 340 is associated with the second axle head 334. Member portion 314 of arm 320 defines a distal end 316 that follows a first direction of elongation Q. Similarly, member portion 344 of arm 340 defines a distal end 346 that also follows a first direction of elongation Q. The joint portion 324 of each arm 320/340 is configured for engagement with the first axle head 333 or the second axle head 334 of the axle 331 and is also configured for placement within the cage assembly 360, as illustrated. In addition, each joint portion 324 includes a curved outer surface 325 defining a plurality of teeth 329 for engagement with the worm gear threading 336 or 337 of the axle 331. As shown, the joint portion 324 of each arm 320/340 includes an arm pivot channel 328 that runs along a second direction of elongation R and is perpendicular to the first direction of elongation Q. When each joint portion 324 is coupled to the cage assembly 360, the arm pivot channel 328 aligns with a respective shoulder pivot channel 374/384 of the cage assembly 360. As shown, the expandable interbody cage device 300 includes the plurality of pivot screws 399 that each secures a respective arm 320/340 to the cage assembly 360 while still enabling rotation of each arm 320/340 about a respective pivot screw 399 in the opposite clockwise or counterclockwise directions A and B. As illustrated, each arm 320/340 can include a bone graft port 322 for insertion of bone graft material for improved fusion of the joint.

Figure 21:
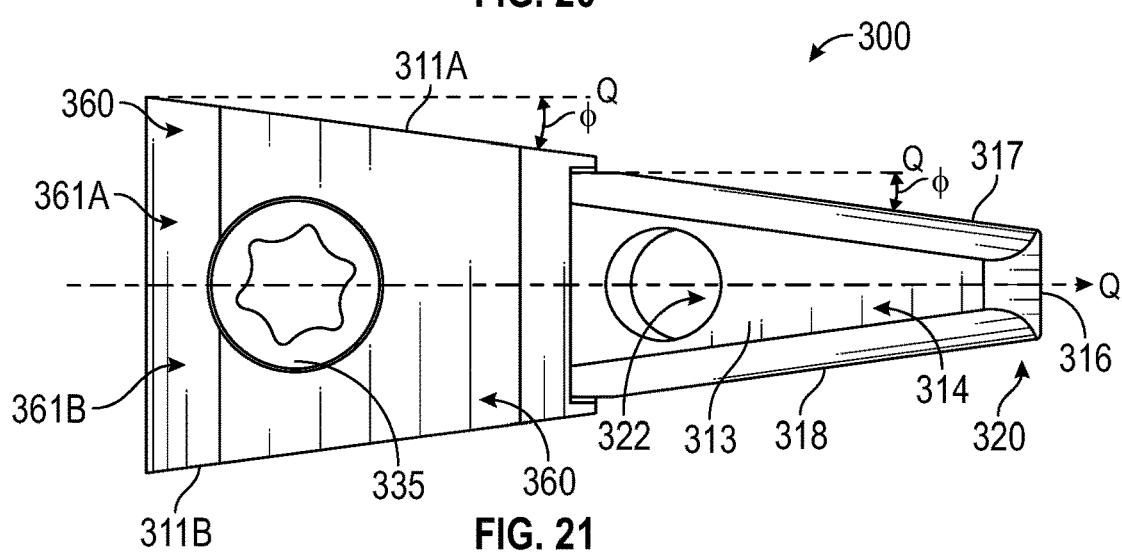
FIG. 21 is a side view of the expandable interbody cage device of FIG. 19 shown in the open configuration.

As discussed above, the member portion 314 of each arm 320/340 follows the first direction of elongation Q and defines a respective distal end 316, a first planar surface 317, and an opposite second planar surface 318 as shown in FIG. 21. Each first planar surface 317/347 and each opposite second planar surface 318 of the arms 320/340 align with respective outer planar surfaces 311A and 311B of the cage assembly 360 to engage the endplate. In the embodiment of FIG. 21, the first planar surface 317 and the opposite second planar surface 318 each define an angle φ relative to a direction of elongation of the member portion 314 of each arm 320/340. As further illustrated, in some embodiments, the member portion 314/344 of each arm 320/340 includes a respective inner planar surface 312/338 and an opposite external planar surface 313/339. When in the closed configuration, the inner planar surface 312/338 of each arm 320/340 is positioned within a respective pocket 350/351 of the cage assembly 360 along the direction of elongation Q of each member portion 314/344 positioned parallel along the direction of elongation X of the axle 331.

When the expandable interbody cage device 300 is in the open configuration, the direction of elongation Q of each arm 320/340 forms a nonzero angle relative to the direction of elongation X of the axle 331. In particular, to transition from the closed configuration to the open configuration, the axle 331 is operable for manual or machine-driven rotation about the direction of elongation X in the clockwise or counterclockwise direction C or D. Rotation of the axle 331 and associated worm gear threads 336 and 337 of the axle 331 causes each arm 320/340 of the plurality of arms 305 to pivot about their respective pivot screws 399 such that the distal portion 316 of each respective arm 320/340 of the plurality of arms 305 is directed away from the axle 331. The continuous nature of the worm threading associated with the axle 331 and each respective arm 320/340 enables each arm 320/340 to be positioned at an angle θ that is variable between 0 to 90 degrees relative to the direction of elongation X of the axle 331 to accommodate differences in anatomy. In some embodiments, the expandable interbody cage device 300 includes one or more bone graft ports 322 associated with each arm 324/340 for packing bone graft material into the opened expandable interbody cage device 300.

Figure 22:
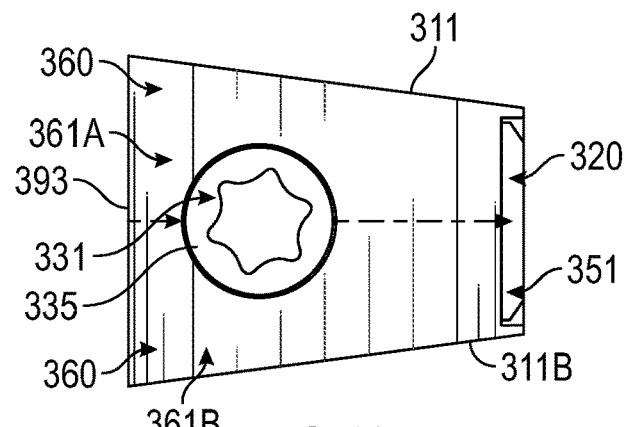
FIG. 22 is a side view of the expandable interbody cage device of FIG. 19 shown in the closed configuration.

In some embodiments, the cage assembly 360 of the expandable interbody cage device 300 can be manufactured in at least two parts. As shown in FIGS. 21 and 22, in some embodiments the cage assembly 360 includes a first cage portion 361A and an opposite second cage portion 361B that collectively form the cage assembly 360. The first and second cage portions 361A and 361B also collectively encapsulate the axle 331. In some embodiments, each cage portion 361A and 361B includes a first cage head 371 and an opposite second cage head 372 which are each respectively configured to receive the first axle head 333 and the second axle head 334 of the axle 331. The first and second cage heads 371 and 372 each engage a respective first arm 320 and a second arm 340 as specifically shown in FIG. 23. Assembly of the expandable interbody cage device 300 is illustrated in terms of the second cage portion 361B and the first cage portion 361A being oriented facedown and coupled with the second cage portion 361B to encapsulate the axle 331 and the joint portions 324/354 of each arm 320/340.

Figure 23:
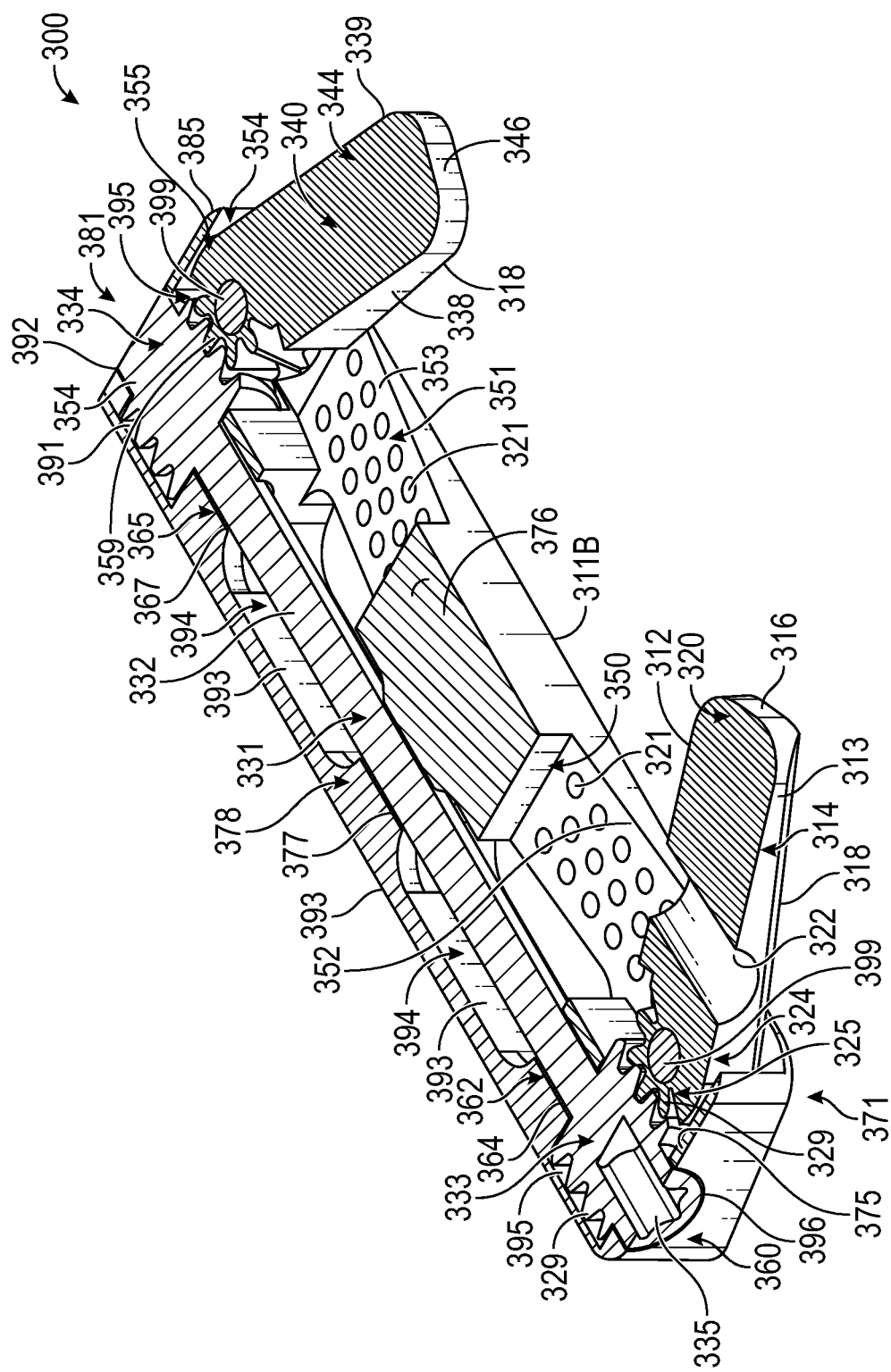
FIG. 23 is a cross-sectional view of the expandable interbody cage device of FIG. 19 taken along line 23-23 of FIG. 19.
Figure 24:
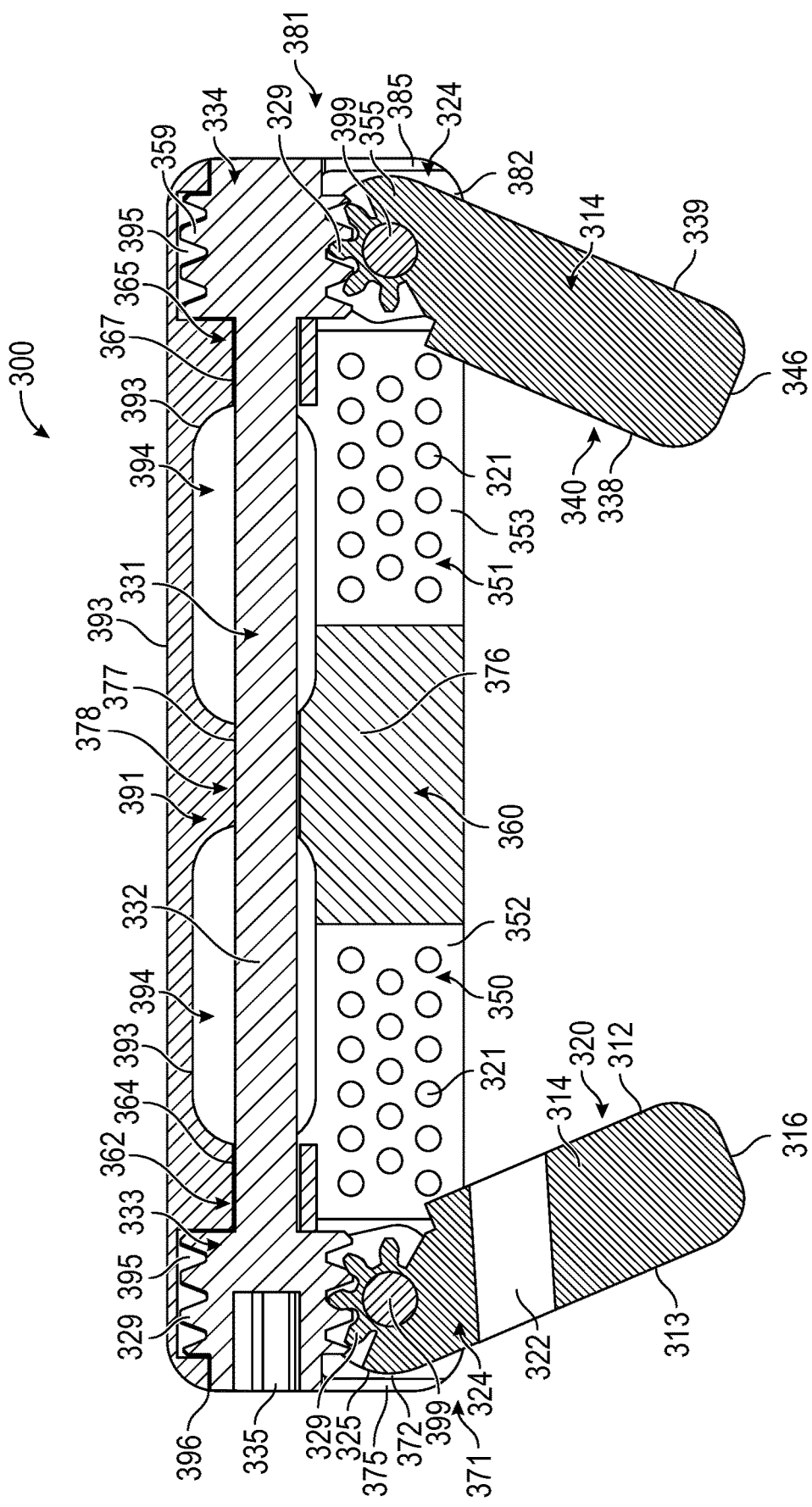
FIG. 24 is a cross-sectional view of the expandable interbody cage device taken along line 24-24 of FIG. 19.

As shown specifically with the cage portion 361B in FIG. 23, the first cage head 371 defines a first shoulder 372 that is directly adjacent to a first seat 395. The first shoulder 372 is configured to receive the first arm 320. As shown, the first shoulder 372 defines an inner surface 373 and a shoulder pivot channel 374 defined through the inner surface 373 to communicate with an outer planar surface 311 of each cage portion 361A/361B. The inner surface 373 and the shoulder pivot channel 374 are collectively configured to engage a joint portion 324 of the first arm 320. The first shoulder 372 further defines a first lip 375 having a direction of elongation that is perpendicular to the inner surface 173 of the left shoulder 172. The first seat 395 defines a depression within the first head 371 and is configured to receive a first axle head 333 of axle 331. A first notch 396 is located adjacent to the first lip 375 and in association with the first seat 395 and permit access to the axle 331 to enable manual or powered rotation of the axle 331 when the axle 331 is seated within each cage portion 361A/361B.

Similarly, the second cage head 381 defines a second shoulder 382 that is directly adjacent to a second seat 391. The second shoulder 382 is configured to receive the second arm 340. As shown, the second shoulder 382 defines an inner surface 383 and a shoulder pivot channel 384 defined through the inner surface 383 to communicate with the outer planar surface 311 of each cage portion 361A/361B. The inner surface 383 and the shoulder pivot channel 384 are collectively configured to engage a joint portion 354 of the second arm 340. The second shoulder 382 further defines a second lip 385 having a direction of elongation that is perpendicular to the inner surface 183 of the second shoulder 182. The second seat 391 defines a depression within the second head 381 and is configured to receive a second axle head 334 of axle 331. A second notch 392 is located adjacent to the second lip 385 and in association with the second seat 391 and enables access to the axle 331 to enable manual or powered rotation of the axle 331 when the axle 331 is seated within each cage portion 361A/361B.

Each cage portion 361A/361B further includes at least a first neck portion 362 defining an axle channel 364 formed axially along a direction of elongation of each respective cage portion 361A/361B for receipt of a shaft 332 of the axle 331. In some embodiments, each cage portion 361A/361B defines a first pocket 350 for receipt of the member portion 314 of first arm 320. Additionally, each cage portion 361A/361B includes at least a central neck portion 378 defining an axle channel 377 formed axially along the direction of elongation of the cage portion 361A/361B for receipt of the shaft 332 of the axle 331. In some embodiments, each cage portion 361A/361B defines the central pillar 376 located between the first arm 320 and a second arm 340 that provides structural support to the cage assembly 360. Further, in the embodiment of FIG. 23, each cage portion 361A/361B further includes a second neck portion 365 in association with the second head 381 and defining an axle channel 367 along a direction of elongation of each cage portion 361A/361B for receipt of the shaft 332 of the axle 331. In some embodiments, the cage portion 361A/361B defines the second pocket 351 for receipt of the member portion 344 of the second arm 340. As shown, each cage portion 361A/361B defines a sidewall surface 393 opposite to the first and second pockets 350 and 351.

As shown and as discussed above, the first planar surface 317 and the opposite second planar surface 318 of each arm 320/340 align with the outer planar surfaces 311A and 311B of the cage assembly 360 to engage the endplate. In the embodiment of FIG. 21, the first planar surface 317 and the opposite second planar surface 318 each define a tapered profile such that a lordotic angle 2*ϕ is defined relative to the direction of elongation Q of the member portion 314 of each arm 320/340. The first outer planar surface 311A and the opposite second outer planar surface of the cage assembly 360 also define the lordotic angle 2*ϕ relative to a direction of elongation of the member portion 314 of each arm 320/340. This arrangement with the first and second outer planar surfaces 311A and 311B and the arms 320 and 340 at the lordotic angle 2*ϕ induces lordosis of the joint to be fused.

In some embodiments, the pockets 350 and 351 each include an associated pocket surface 352 and 353. As shown, each pocket surface 352/353 can be angled to fit the grade of the associated arm 320/340. In some embodiments, each pocket surface 352/353 includes a plurality of perforations 321 that allow bone graft material packed within the expandable interbody cage device 300 to grow onto the endplate surface below and above the expandable interbody cage device 300. In addition, each pocket 350/351 communicates with a respective bone graft cavity 394 associated with the axle 331, as shown, in which bone graft material can be packed. Bone graft material can be packed in the bone graft cavities 394 and can also packed in through the bone graft port 322 of an associated arm 320/340.

It should be understood from the foregoing that, while particular embodiments have been illustrated and described, various modifications can be made thereto without departing from the spirit and scope of the invention as will be apparent to those skilled in the art. Such changes and modifications are within the scope and teachings of this invention as defined in the claims appended hereto.

What is claimed is:

1. An expandable interbody cage device, comprising:
    an axle including a first axle head and an opposite second axle head,
        wherein the first axle head defines a first worm threading and wherein the second axle head defines an opposite second worm threading,
        wherein the axle is rotatable about a direction of elongation of the axle in a first direction C or an opposite second direction D;
    a plurality of arms in association with the axle, including:
    a first arm in association with the first axle head, wherein the first arm includes a joint portion and a member portion, wherein the first arm is rotatable in a first direction A or an opposite second direction B about the joint portion by the first axle head of the axle, and wherein the first arm defines a first planar surface configured to contact a cortical bone surface of a first vertebra and an opposite second planar surface configured to contact a cortical bone surface of a second vertebra; and
    a second arm in association with the opposite second axle head, wherein the second arm includes a joint portion and a member portion, wherein the second arm is rotatable in the first direction A or the opposite second direction B about the joint portion by the opposite second axle head of the axle, and wherein the second arm defines a first planar surface configured to contact the cortical bone surface of the first vertebra and an opposite second planar surface configured to contact the cortical bone surface of the second vertebra; and
    a cage assembly encapsulating the axle and the joint portion of the first arm and the joint portion of the second arm, wherein the cage assembly includes a first external planar surface configured to contact an endplate surface of the first vertebra and an opposite second external planar surface configured to contact an endplate surface of the second vertebra.

2. The expandable interbody cage device of claim 1 wherein the expandable interbody cage device is operable to assume a closed configuration, wherein a direction of elongation of each member portion of the first arm and the second arm is parallel with the direction of elongation of the axle.

3. The expandable interbody cage device of claim 1, wherein the expandable interbody cage device is operable to assume an open configuration wherein a direction of elongation of each member portion of the first arm and the second arm forms an angle θ that is variable between 0 to 90 degrees relative to the direction of elongation of the axle.

4. The expandable interbody cage device of claim 1, wherein a distal portion of each of the first arm and the second arm of the plurality of arms is extended beyond the cage assembly when in an open configuration such that the member portion of each of the first arm and the second arm engages the respective cortical bone surface.

5. The expandable interbody cage device of claim 1, wherein the joint portion of the first arm and the second arm defines a curved outer surface and a plurality of teeth thereon, wherein the first arm plurality of teeth is configured for engagement with the first worm threading of the first axle head and the second arm plurality of teeth is configured for engagement with the opposite second worm threading of the opposite second axle head.

6. The expandable interbody cage device of claim 1, wherein the cage assembly defines a first cage head configured to receive the first axle head, and a second cage head configured to receive the opposite second axle head.

7. The expandable interbody cage device of claim 6, wherein the first cage head is configured to receive the joint portion of the first arm in association with the first axle head and wherein the second cage head is configured to receive the joint portion of the second arm in association with the opposite second axle head.

8. The expandable interbody cage device of claim 1, wherein the cage assembly includes a cavity for receipt of bone graft material.

9. The expandable interbody cage device of claim 1, further defining a void between the first arm or the second arm of the plurality of arms and the cage assembly when the expandable interbody cage device is in an open configuration.

10. The expandable interbody cage device of claim 9, wherein the void is operable to be packed with bone graft material.

11. The expandable interbody cage device of claim 9, wherein the first arm or the second arm of the plurality of arms includes a bone graft port.

12. The expandable interbody cage device of claim 1, further comprising a third arm of the plurality of arms in association with the first axle head and a fourth arm of the plurality of arms in association with the opposite second axle head.

13. The expandable interbody cage device of claim 1, wherein the cage assembly, the first arm and the second arm each define a tapered profile having an angle φ relative to a direction of elongation Q of the member portion of the first arm and the second arm of the plurality of arms, wherein each tapered profile is configured to induces lordosis between the first and second vertebrae at the lordotic angle that correlates with the angle φ defined by the tapered profile when the expandable interbody cage device is positioned between the first and second vertebrae.

14. A method, comprising:
    providing an expandable interbody cage device, comprising:
    an axle including a first axle head having a first threading and an opposite second axle head having an opposite second threading, wherein the axle is rotatable about a direction of elongation X of the axle in a first direction C or an opposite direction D; and
    a plurality of arms in association with the axle, including:
    a first arm in association with the first axle head, wherein the first arm includes a joint portion and a member portion and wherein the first arm is rotatable in a first direction A or an opposite second direction B about the joint portion by the first axle head of the axle; and
    a second arm in association with the opposite second axle head, wherein the second arm includes a joint portion and a member portion, wherein the second arm is rotatable in the first direction A or the opposite second direction B about the joint portion by the opposite second axle head of the axle;

wherein the expandable interbody cage device is operable to assume a closed configuration and an open configuration;

inserting the expandable interbody cage device between a first endplate surface of a first vertebra and a second endplate surface of a second vertebra; and rotating the axle in the first direction C or the opposite direction D such that each arm of the plurality of arms is resultantly rotated in the first direction A or the opposite second direction B such that the expandable interbody cage device assumes the open configuration.

15. The method of claim 14, wherein in the closed configuration, a direction of elongation Q of each member portion is parallel with the direction of elongation X of the axle and wherein in the open configuration, the direction of elongation Q of each member portion forms an angle that is variable between 0 to 90 degrees relative to the direction of elongation X of the axle.

16. The method of claim 14, wherein the first arm defines a first planar surface configured to contact a cortical bone surface of the first vertebra and an opposite second planar surface configured to contact a cortical bone surface of the second vertebra and wherein the second arm defines a first planar surface configured to contact the cortical bone surface of the first vertebra and an opposite second planar surface configured to contact the cortical bone surface of the second vertebra.

17. The method of claim 14, wherein the expandable interbody cage device further comprises a cage assembly encapsulating the axle and the joint portion of the first arm and the joint portion of the second arm, wherein the cage assembly includes a first external planar surface configured to contact the first endplate surface of the first vertebra and an opposite second external planar surface configured to contact the second endplate surface of the second vertebra.

18. The method of claim 17, further comprising: inserting bone graft material into a void defined between the first arm or the second arm of the plurality of arms and the cage assembly when the expandable interbody cage device is in an open configuration.

19. The method of claim 14, wherein the expandable interbody cage device is in a closed configuration during insertion.

* * * * *